United States Patent
Shaw

(10) Patent No.: US 10,906,871 B2
(45) Date of Patent: Feb. 2, 2021

(54) PROCESSES FOR MAKING, AND METHODS OF USING, GLYCOPYRRONIUM COMPOUNDS

(71) Applicant: Dermira, Inc., Menlo Park, CA (US)

(72) Inventor: Anthony Adrian Shaw, Redwood City, CA (US)

(73) Assignee: Dermira, Inc., Menlo Park, CA (US)

( * ) Notice: Subject to any disclaimer, the term of this patent is extended or adjusted under 35 U.S.C. 154(b) by 0 days.

(21) Appl. No.: 16/320,999

(22) PCT Filed: Aug. 1, 2017

(86) PCT No.: PCT/US2017/044988
§ 371 (c)(1),
(2) Date: Jan. 25, 2019

(87) PCT Pub. No.: WO2018/026869
PCT Pub. Date: Feb. 8, 2018

(65) Prior Publication Data
US 2019/0161443 A1    May 30, 2019

Related U.S. Application Data

(60) Provisional application No. 62/370,172, filed on Aug. 2, 2016.

(51) Int. Cl.
*C07D 207/12*    (2006.01)
*C07B 57/00*    (2006.01)
*A61P 43/00*    (2006.01)

(52) U.S. Cl.
CPC ............ *C07D 207/12* (2013.01); *C07B 57/00* (2013.01); *A61P 43/00* (2018.01); *C07B 2200/07* (2013.01)

(58) Field of Classification Search
None
See application file for complete search history.

(56) References Cited

U.S. PATENT DOCUMENTS

2007/0123557 A1    5/2007    Bodor

FOREIGN PATENT DOCUMENTS

| CN | 104586841 A | 5/2015 |
|---|---|---|
| WO | WO 03/087094 A2 | 10/2003 |

OTHER PUBLICATIONS

International Search Report and Written Opinion of PCT/US2017/044988 dated Dec. 11, 2017, 17 pages.

*Primary Examiner* — Samantha L Shterengarts
(74) *Attorney, Agent, or Firm* — Squire Patton Boggs (US) LLP

(57) ABSTRACT

Provided herein are processes for making and methods of using salts of glycopyrronium, including solid forms and forms suitable for use as topicals. Disclosed here are processes for making salts of glycopyrronium, also processes for making compositions comprising salts of glycopyrronium, and methods of treating hyperhidrosis with salts of glycopyrronium as well as with compositions comprising salts of glycopyrronium such as, but not limited to, topical compositions. Disclosed herein are methods of treating hyperhidrosis including administering salts of glycopyrronium to subjects in need thereof.

37 Claims, 4 Drawing Sheets

PROCESSES FOR MAKING, AND METHODS OF USING, GLYCOPYRRONIUM COMPOUNDS

CROSS-REFERENCE TO RELATED APPLICATIONS

This application claims the benefit of priority to International PCT Patent PCT/US2017/044988, filed Aug. 1, 2017, which claims the benefit of priority to U.S. Provisional Patent Application No. 62/370,172, filed Aug. 2, 2016, the entire content of each of which is herein incorporated by reference in its entirety for all purposes.

FIELD

The present disclosure sets forth synthetic processes and chemical reagents for making glycopyrronium salts, stereospecifically and stereoselectively, including particular stereoisomers and mixtures of stereoisomers in high yield and with high selectivity. Also set forth herein are derivatives and analogs of glycopyrronium salts.

BACKGROUND

Certain glycopyrronium salts and related compounds, as well as processes for making and methods of using these glycopyrronium salts and related compounds, are known. See, for example, U.S. Pat. No. 8,558,008, which issued to assignee Dermira, Inc. See also, for example, U.S. Pat. No. 2,956,062, which issued to assignee Robins Co Inc. A H. See also, for example, International Patent Application Publication Nos. WO 98/00132 A1 and WO 2009/00109A1, both of which list applicant Sepracor, Inc., as well as U.S. Pat. Nos. 6,063,808 and 6,204,285, both of which issued to assignee Sepracor, Inc. Certain methods of treating hyperhidrosis using glycopyrronium salts and related compounds are known. See, for example GB 1,080,960. Certain forms of applying glycopyrrolate compounds to a subject are known. See, for example U.S. Pat. Nos. 6,433,003 and 8,618,160, both of which issued to assignee Rose U; also U.S. Pat. Nos. 7,060,289; 8,252,316; and 8,679,524, which issued to PurePharm, Inc.

One glycopyrronium salt which is useful in certain medical applications is the following compound:

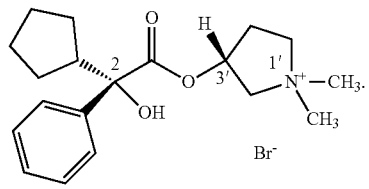 [SMILES: C[N+]1(C)CC[C@@H](OC(=O)[C@@](O)(c2ccccc2)C2CCCC2)C1 ; [Br-]]

As illustrated above, the absolute configuration at the three asymmetric chiral positions is 2R3'R1'RS. This means that the carbon indicated with the number, 2, has the stereochemical R configuration. The carbon indicated with the number, 3', also has the stereochemical R configuration. The quaternary ammonium nitrogen atom, indicated with a positive charge, may have either the R or the S stereochemical configuration. As drawn, the compound above is a mixture of two diastereoisomers.

Certain processes for making glycopyrronium salts are known. However, these processes are not as safe, efficient, stereospecific, or stereoselective as the new processes disclosed herein, for example with respect to large-scale manufacturing processes. Certain publications show that higher anticholinergic activity is attributed to the 2R3'R configuration. However, to date, processes for making the 2R3'R isomers, as well as the 2R3'R1'R isomers are low yielding, involve too many reaction steps to be economically feasible, use toxic materials, and/or are not sufficiently stereospecific or stereoselective with respect to the products formed.

SUMMARY

In one embodiment, set forth herein is a process for making a compound of Formula (I):

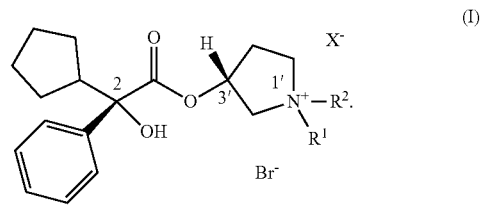

wherein:

$R^1$ and $R^2$ are each, independently in each instance, selected from alkyl and alkyl substituted with alkoxycarbonyl;

the stereochemical configuration about the carbon atom indicated by 2 is R;

the stereochemical configuration about carbon atom indicated by 3' is R;

$X^-$ is an anion;

wherein the process includes step (1) contacting a compound of Formula (Ia) with a compound of Formula (Ib) under coupling conditions to form a compound of Formula (Ic):

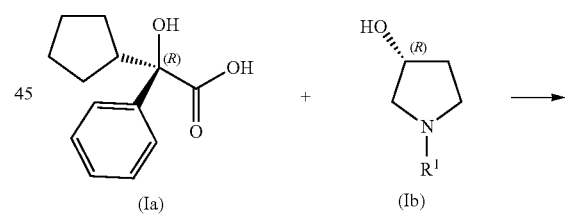

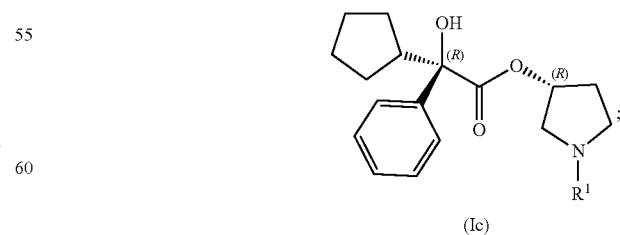

and step (2) contacting a compound of Formula (Ic) with a compound of Formula (Id) to make a compound of Formula (I):

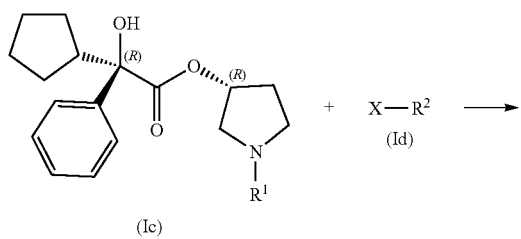 +  → 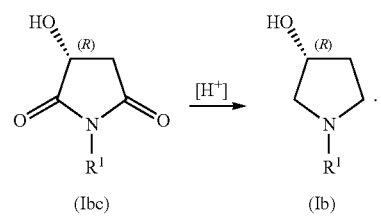

(Ic)    (Id)

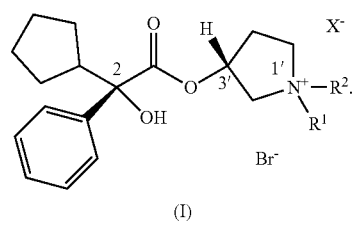

(I)

In a second embodiment, set forth herein is a process for making a compound of Formula (Ib):

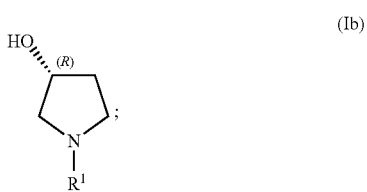

(Ib)

In some embodiments, $R^1$ is selected from alkyl and alkyl substituted with alkoxycarbonyl.

In some embodiments, the process includes step (1): providing a compound (5):

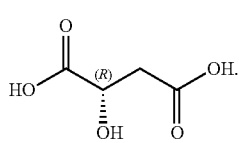

(5)

In some embodiments, the process includes step (2): contacting compound (5) with an alkyl-amine (e.g., $R^1$—$NH_2$) to form a compound of Formula (Ibc):

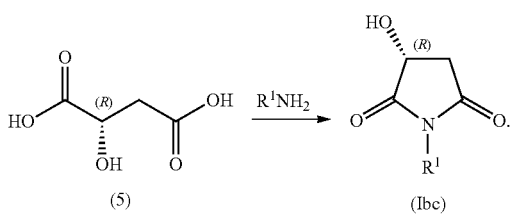

(5)        (Ibc)

In some embodiments, the process includes contacting compound of Formula (Ibc) with reducing agent (indicated by [H$^+$], below) to form a compound of Formula (Ib):

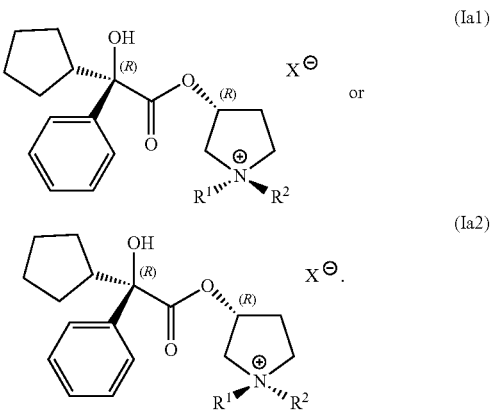

(Ibc)        (Ib)

In a third embodiment, set forth herein is a composition including a mixture of compounds having following structures (Ia1) and (Ia2):

(Ia1)

or (Ia2)

In some embodiments, the compounds having structures (Ia1) and (Ia2) are prepared by a process disclosed herein. In some embodiments, the compounds are formulated with a pharmaceutically acceptable excipient, diluent, or salt. $R^1$ $R^2$, and $X^-$ are as defined above for Formula (I).

In a fourth embodiment, set forth herein is a process for treating hyperhidrosis, including administering to a subject in need thereof a composition comprising a compound prepared by a process disclosed herein or a composition disclosed herein.

In a fifth embodiment, set forth herein is a method of treating a disease or disorder marked by a need for an anticholinergic agent, including administering to a subject in need thereof a composition comprising a compound prepared by a process disclosed herein or a composition disclosed herein.

BRIEF DESCRIPTIONS OF THE DRAWINGS

DETAILED DESCRIPTION

Figure 1:
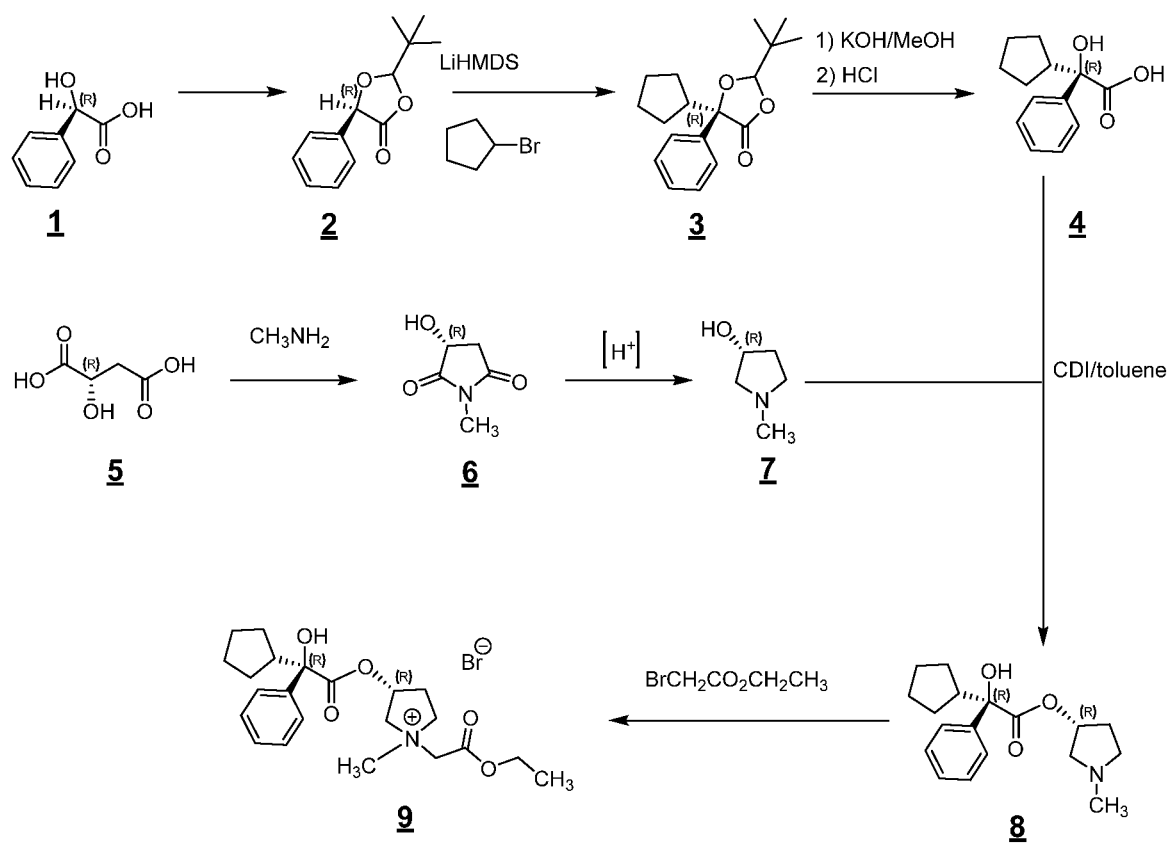
FIG. 1 shows an example synthesis for making a glycopyrronium salt.

Set forth herein are processes for making compounds having two stereocenters with the stereochemical R configuration. For example, set forth herein are processes for making glycopyrronium salts, including but not limited to, coupling cyclopentylmandelic acid (CPMA) (or an ester derivative thereof) to 1-methyl-3-hydroxypyrrolidine (NMHP) followed by alkylation at the 1'-position of the resulting glycopyrronium base (GPB), using an alkylating agent, such as, but not limited to, ethyl bromoacetate. In some examples, set forth herein is an efficient process for coupling 2-(R)-CPMA with 3-(R)-NMHP to make a 2R3'R-GPB directly, followed by alkylation at the N1' position.

A. DEFINITIONS

As used herein, the term "yield," refers to the empirical yield for a given chemical reaction. Yield is a percent which represents the extent to which a reaction proceeded to produce a given product. Percent yield is calculated by assuming a chemical reaction and assuming that all of the chemical reagents react and become products, limited only by the limiting reagent wherein the limiting reagent is the reagent which is consumed first as the reaction proceeds. This initial calculation produces what is known as the theoretical yield. Once the reaction is empirically performed, the products are analyzed. The amounts of products may be massed, determined spectroscopically, or determined by other empirical means. The amount of products massed, determined spectroscopically, or determined by other empirical means represents the empirical yield. "Yield" as used herein and in the claims refers to the quotient of the empirical yield over the theoretical yield, and then multiplied by 100. For example, in the reaction A+2B→C, if one has 1 mole of A and 1 mole of B, then B is the limiting reagent since 2 moles of B are needed to react with 1 mole of A. According to the reaction example, 1 mole of B will produce 0.5 moles of C. If 1 mole of A reacts with 1 mole of B, and one determines empirically that 0.4 moles of C were produced, then the theoretical yield would be 0.5 moles, and the empirical yield would be 0.4 moles. The percent yield would be therefore be 80% since (0.4/0.5) (100)=80%.

As used herein, the term "alkyl" refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, butyl, a pentyl moiety, a hexyl moiety, cyclopropyl, cyclobutyl, cyclopentyl, and cyclohexyl.

As used herein, the term "cycloalkyl" refers to a cyclic alkyl. Cycloalkyl is optionally substituted. Examples of cycloalkyl moieties include, but are not limited to, cyclopropyl, cyclobutyl, cyclopentyl, cyclohexyl, cycloheptyl, and cyclooctyl.

As used herein, "alkoxy" refers to a monovalent and saturated hydrocarbon radical moiety wherein the hydrocarbon includes a single bond to an oxygen atom and wherein the radical is localized on the oxygen atom, e.g. $CH_3CH_2$—O for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, the term "alkoxycarbonyl," refers to a monovalent and saturated hydrocarbon radical moiety wherein the hydrocarbon includes a single carbon bond to an oxygen atom, which is further bonded to a carbonyl, e.g., C(O). The oxygen atom is a bivalent atomic linker between the alkyl portion of the alkoxycarbonyl and the carbonyl. The radical in alkoxycarbonyl is localized on the carbon atom of the carbonyl which is bonded to an oxygen atom of an alkoxy e.g. $CH_3CH_2$—O—C·(O). Alkoxycarbonyl substituents bond to the compound which they substitute through this carbonyl carbon atom. Alkoxycarbonyl is optionally substituted and can be linear or branched. Alkoxycarbonyl includes, but is not limited to, those having 1-20 carbon atoms, i.e., $C_{1-20}$ alkoxycarbonyl; 1-12 carbon atoms, i.e., $C_{1-12}$ alkoxycarbonyl; 1-8 carbon atoms, i.e., $C_{1-8}$ alkoxycarbonyl; 1-6 carbon atoms, i.e., $C_{1-6}$ alkoxycarbonyl; and 1-3 carbon atoms, i.e., $C_{1-3}$ alkoxycarbonyl. Examples of alkoxy moieties include, but are not limited to methoxycarbonyl, and ethoxycarbonyl.

As used herein, the term "halo" refers to a halogen substituent. Halogen substituents include fluoro, chloro, bromo, and iodo.

As used herein, the phrase "using a salt-resolution procedure," refers to a process for using a salt, e.g., 5-nitroisophthalate salt, to isolate or purify one stereoisomer from a mixture of stereoisomers, e.g., mixtures of diastereomers. Exemplary processes for using a salt-resolution procedure are set forth in Finnish Patent 49713, which issued Sep. 10, 1975 and which was filed May 15, 1974.

As used herein, the phrase "coupling conditions," refers to reaction conditions and reactions which are suitable to bond two compounds together, or which catalyze the bonding of two compounds together. For example, U.S. Pat. No. 9,006,462, which issued to Dermira, Inc., sets forth example coupling conditions which include reagents such as but not limited to 1,1-carbonyldiimidazole in toluene.

As used herein, the phrase "stereomerically pure," refers to a particular stereoisomer of a compound which is present to a greater extent than other stereoisomers of that compound, e.g., the compound is present in diastereomeric excess or the compound is present in enantiomeric excess. In some embodiments, the stereomerically pure compounds described herein include 80% or greater, 85% or greater, 90% or greater, 95% or greater, or 97% or greater by weight of one stereoisomer of the compound. In some embodiments, the stereomerically pure compounds described herein include 80% or greater, 85% or greater, 90% or greater, 95% or greater, or 97% or greater by mole of one stereoisomer of the compound.

As used herein, the term "anion," refers to a negatively charged atom or molecule, e.g., a halide or a tosylate. Herein, anion includes a species which charge balances the positively charged species to which the anion is associated or paired. For example, some salts provided herein include a positively charged quaternary ammonium group. This positively charged quaternary ammonium group forms a neutrally charged salt by bonding ionically to an anion(s), such as but not limited to, fluoride, chloride, bromide, iodide, benzoate, edisylate, oxalate, hydrogen sulfate, and tosylate.

B. PROCESS FOR MAKING GLYCOPYRRONIUM SALTS

In certain examples, set forth here is a process for making a compound of Formula (I):

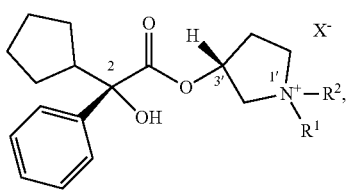

(I)

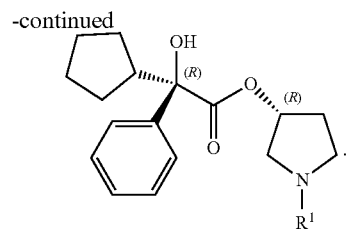

(Ic)

In Formula (I), $R^1$ and $R^2$ are each, independently in each instance, selected from alkyl and alkyl substituted with alkoxycarbonyl;

the stereochemical configuration about the carbon atom indicated by 2 is R;

the stereochemical configuration about carbon atom indicated by 3' is R; and $X^-$ is an anion.

In some of these examples, $R^1$ is alkyl. In other examples, $R^1$ is methyl, ethyl, n-propyl, i-propyl, n-butyl, t-butyl, i-butyl, n-pentyl, or i-pentyl. In some examples, $R^1$ is methyl or ethyl. In some other examples, $R^1$ is methyl. In other examples, $R^1$ is ethyl.

In some examples, $R^2$ is alkyl. In some examples, $R^2$ is methyl, ethyl, n-propyl, i-propyl, n-butyl, t-butyl, i-butyl, n-pentyl, or i-pentyl. In certain examples, $R^2$ is methyl or ethyl. In some examples, $R^2$ is methyl. In other examples, $R^2$ is ethyl. In some examples, both $R^1$ and $R^2$ are methyl.

In some of these examples, $R^1$ is alkyl. In some examples, $R^1$ is methyl, ethyl, n-propyl, i-propyl, n-butyl, t-butyl, i-butyl, n-pentyl, or i-pentyl. In certain examples, $R^1$ is methyl or ethyl. In some examples, $R^1$ is methyl. In other examples, $R^1$ is ethyl. In any of these examples in this paragraph, $R^2$ is alkyl. In some examples, $R^2$ is methyl, ethyl, n-propyl, i-propyl, n-butyl, t-butyl, i-butyl, n-pentyl, or i-pentyl. In certain examples, $R^2$ is methyl or ethyl. In some examples, $R^2$ is methyl. In other examples, $R^2$ is ethyl. In some examples, both $R^1$ and $R^2$ are methyl.

In some of the examples herein, $R^1$ is alkyl substituted with alkoxycarbonyl. In some examples, $R^1$ is methyl substituted with alkoxycarbonyl. In some examples, $R^1$ is —CH$_2$C(O)OCH$_2$CH$_3$. In some of the examples in this paragraph, $R^2$ is alkyl. In certain examples, $R^2$ is methyl or ethyl. In some examples, $R^2$ is methyl. In other examples, $R^2$ is ethyl.

In certain examples, the processes for making a compound of Formula (I) include step (1): contacting a compound of Formula (Ia) with a compound of Formula (Ib) under coupling conditions to form a compound of Formula (Ic):

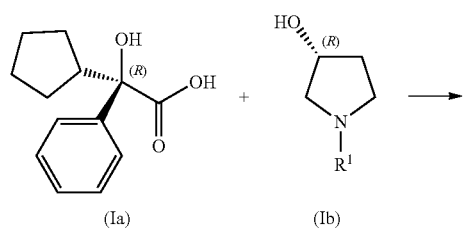

In some examples, compound (Ia) is treated with one equivalent of carbonyldiimideazole (CDI) in toluene at ambient temperature and allowed to react under agitation for 1-2 hours to form an activated form of compound (Ia). In some examples, approximately one equivalent of compound (Ib) is added to the activated form of compound (Ia). In certain examples, the reaction mixture is further warmed to about 70° C. In some examples, the reaction mixture is further agitated. In some examples, the agitation is maintained until the reaction is complete as measured by monitoring the disappearance or consumption of compound (Ib) or of the activated form of compound (Ia). In some examples, the reaction is complete in 1, 2, 3, 4, 5, 6, 7, 8, 9, 10, 11, or 12 hours. In some examples, the reaction is complete within 6-8 hours. In some examples, the processes herein further include washing the toluene-including solution 3-4 times with purified water to remove the imidazole side product. In some examples, the processes further include concentrating the organic phase under vacuum to leave an oil which may be used directly in other processes disclosed herein.

In some examples of the processes for making a compound of Formula (Ic), the reaction is carried out in one or more solvents. The solvent(s) can be any solvent deemed suitable to those of skill in the art for carrying out the reaction. In certain embodiments, the solvent(s) does not appreciably react with the compound of Formula (Ia) or (Ib). In certain embodiments, the solvent(s) is selected from toluene.

In some examples, the solvent is selected from the group consisting of ethers, esters, aromatics, alkanes, chlorinated solvents and ketones. In some examples, the solvent is selected from the group consisting of N-methyl-pyrrolidone (NMP), dimethyl formamide (DMF) and dimethylacetamide (DMAC). In some examples, when the solvent is an ether, the solvent is selected from tetrahydrofuran (THF), methyl tetrahydrofuran (MeTHF), methyl tert-butyl ethyl (MTBE), and combinations thereof. In some examples, when the solvent is an ester, the solvent is selected from ethyl acetate, isopropyl acetate, and combinations thereof. In some examples, when the solvent is an aromatic, the solvent is selected from toluene, chlorobenzene, xylenes, and combinations thereof. In some examples, when the solvent is an alkane, the solvent is selected from pentane, hexane, heptane, and combinations thereof. In some examples, when the solvent is a chlorinated solvent, the solvent is selected from dichloromethane, chloroform, and combinations thereof. In some examples, when the solvent is a ketone, the solvent is selected from methyl ethyl ketone (MEK). In some examples, the solvent in a combination of any of the aforementioned solvents. In some examples, the solvent is a combination of any of the above ethers, esters, aromatics, alkanes, chlorinated solvents and ketone solvents. In some examples, the solvent is selected from NMP, DMF, DMAC, THF, MeTHF, MTBE, ethyl acetate, isopropyl acetate, toluene, chlorobenzene, xylenes, pentane, hexane, heptane, dichloromethane, chloroform, methyl ethyl ketone, and combinations thereof. In some examples, the solvent includes NMP, DMF, DMAC, THF, MeTHF, MTBE, ethyl acetate, isopropyl acetate, toluene, chlorobenzene, xylenes, pentane, hexane, heptane, dichloromethane, chloroform, methyl ethyl ketone, or combinations thereof.

In some examples, the concentration of the compound according to Formula (Ia) or (Ib) is about 0.1M to about 2 M. In some examples, the concentration of the compound according to Formula (Ia) or (Ib) is about 0.1M, 0.2M, 0.3M, 0.4M, 0.5M, 0.6M, 0.7M, 0.8M. 0.9M or 1M. In some examples, the concentration of the compound according to Formula (Ia) or (Ib) is about 0.5M.

In some examples, the processes herein include using an excess of the compound of Formula (Ia) with respect to compound (Ib). In some examples, the processes herein include using about 5% by mole excess of the compound (Ia) with respect to compound (Ib). In some examples, the reaction includes about three times (i.e., 3×) by mole excess of the alkylating agent compound (Ia) with respect to compound (Ib).

The processes for making a compound of Formula (Ic) are carried out at any temperature deemed suitable by those of skill in the art. In particular embodiments, the reaction is conducted at any temperature from about 0° C. to about 80° C., from about 10° C. to about 75° C., from about 20° C. to about 65° C., or from about 30° C. to about 55° C. In particular embodiments, the reaction is at room temperature. In particular embodiments, the reaction is at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., or about 85° C.

The processes for making a compound of Formula (Ic) are carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, or at least about 10,000 L.

The reaction above can proceed for any time deemed suitable for formation of compound (Ic). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography. In certain embodiments, the reaction proceeds in about 6 to about 8 hours. In certain embodiments, the reaction proceeds in about 6 to about 8 hours at 70° C.

In some examples, the reaction progress is monitored by observing the consumption of compounds of Formula (Ia) or (Ib) by either thin-layer chromatograph (TLC) or high-pressure liquid chromatography (HPLC).

In some examples, the processes for making a compound of Formula (I) further include step (2): contacting a compound of Formula (Ic) with a compound of Formula (Id) under coupling conditions to make a compound of Formula (I):

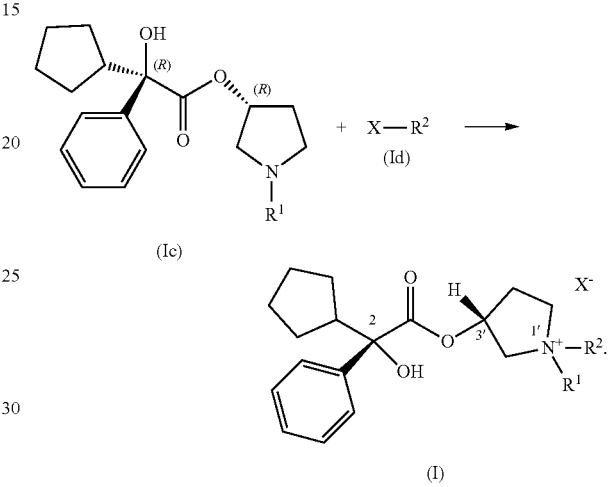

In certain examples the processes for making a compound of Formula (I) further includes using an appropriate solvent at room temperature and a 3-fold excess of compound of Formula (Id) with respect to the compound of Formula (Ic). In some examples, the product compound of Formula (I) may crystallize from the reaction mixture. In some of those examples, wherein the compound of Formula (I) does crystallize, it may be recovered by filtration. In some of the examples herein, the crude product is purified by trituration or recrystallization from an appropriate solvent.

In some examples of the processes for contacting a compound of Formula (Ic) with a compound of Formula (Id) under coupling conditions to make a compound of Formula (I), the reaction is carried out in one or more solvents. The solvent(s) can be any solvent deemed suitable to those of skill in the art for carrying out the reaction. In certain embodiments, the solvent(s) does not appreciably react with the compound of Formula (Ic) or (Id). In certain embodiments, the solvent(s) is selected from acetonitrile. In some examples, the concentration of the compound according to Formula (Ic) or (Id) is about 0.1M to about 2 M. In some examples, the concentration of the compound according to Formula (Ic) or (Id) is about 0.1M, 0.2M, 0.3M, 0.4M, 0.5M, 0.6M, 0.7M, 0.8M, 0.9M or 1M. In some examples, the concentration of the compound according to Formula (Ic) or (Id) is about 0.5M. The compound according to Formula (Id) is used in an amount of at least about 1 equivalents with respect to the compound of Formula (Ic), and in some embodiments about compound (Id) is in at least a 5% molar excess compared to the compound of Formula (Ic). In some embodiments compound (Id) is in at least a 5% molar excess compared to the compound of Formula (Ic). In some examples, compound (Id) is present in 5-15 volumetric portions with respect to compound (Ic). In some examples, the concentration of the compound according to Formula (Id) is present at a concentration of about 0.1M, 0.2M, 0.3M, 0.4M, 0.5M, 0.6M, 0.7M, 0.8M. 0.9M or 1M. In some examples, the concentration of the compound according to Formula (Ic) is about 0.1M, 0.2M, 0.3M, 0.4M, 0.5M, 0.6M, 0.7M, 0.8M. 0.9M or 1M. In some examples, the concentration of the compound according to Formula (Id) is about 0.3M-1M. In some examples, the concentration of the compound according to Formula (Ic) is about 0.3M-1M.

The processes for contacting a compound of Formula (Ic) with a compound of Formula (Id) under coupling conditions to make a compound of Formula (I) are carried out at any temperature deemed suitable by those of skill in the art. In particular embodiments, the reaction is conducted at any temperature from about 0° C. to about 80° C., from about 10° C. to about 75° C., from about 20° C. to about 65° C., or from about 30° C. to about 55° C. In particular embodiments, the reaction is at room temperature. In particular embodiments, the reaction is at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., or about 85° C.

In some examples, the aforementioned reaction is carried out at room temperature. In some examples, this reaction is run at a temperature higher than room temperature, for example, when bulky substituents are present on the reactant compounds.

The processes for contacting a compound of Formula (Ic) with a compound of Formula (Id) under coupling conditions to make a compound of Formula (I) are carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, or at least about 10,000 L.

The reaction above can proceed for any time deemed suitable for formation of compound (I). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography, In some examples, the reaction time will depend on the substituents present on the compound of Formula (Id). In some examples, the reaction time will depend on the reaction temperature. In some examples, the reaction time will depend on the molar excess of compound (Id) with respect to compound (Ic). In certain examples, the reaction is complete at room temperature in about 3 hours when compound (Id) is ethyl bromoacetate.

Also described herein are processes for monitoring the reaction progress, including, but not limited to, monitoring the residual amount of compound (Id) or (Ic) by thin layer chromatography (TLC), gas chromatography (GC) by high-pressure liquid chromatograph (HPLC). In some examples, the monitoring the reaction progress is by TLC. In some examples, the monitoring the reaction progress is by GC. In some examples, the monitoring the reaction progress is by HPLC.

In certain examples, the processes for making a compound of Formula (I) further include step (3): isolating a stereomerically pure stereoisomer of a compound of Formula (I). In some examples, the stereomerically pure stereoisomer of a compound of Formula (I) is present in an enantiomeric excess of at least 80%. In some examples, the stereomerically pure stereoisomer of a compound of Formula (I) is present in an enantiomeric excess of at least 85%. In some examples, the stereomerically pure stereoisomer of a compound of Formula (I) is present in an enantiomeric excess of at least 90%. In some examples, the stereomerically pure stereoisomer of a compound of Formula (I) is present in an enantiomeric excess of at least 95%. In some examples, the stereomerically pure stereoisomer of a compound of Formula (I) is present in an enantiomeric excess of at least 99%. In some examples, the stereomerically pure stereoisomer of a compound of Formula (I) is present in an diastereomeric excess of at least 80%. In some examples, the stereomerically pure stereoisomer of a compound of Formula (I) is present in an diastereomeric excess of at least 85%. In some examples, the stereomerically pure stereoisomer of a compound of Formula (I) is present in an diastereomeric excess of at least 90%. In some examples, the stereomerically pure stereoisomer of a compound of Formula (I) is present in an diastereomeric excess of at least 95%. In some examples, the stereomerically pure stereoisomer of a compound of Formula (I) is present in an diastereomeric excess of at least 99%.

In some examples, the processes for making a compound of Formula (I) further include isolating a compound of Formula (I) by column chromatography. In some of these examples, the isolating of a compound of Formula (I) is by column chromatography. In some examples, the processes for making a compound of Formula (I) further include isolating a compound of Formula (I) using the relative solubility of the 5-nitroisophthalate salt of a compound of Formula (I). For example, in some examples, the processes for making a compound of Formula (I) include making the 2R3'R1' of a compound of Formula (I). For example, in some examples, the processes for making a compound of Formula (I) include making the 2R3'S1' of a compound of Formula (I). Based on this difference in solubility, the threo pair can be separated from the erythro pair, e.g., by precipitating the low solubility pair and washing away the higher solubility pair.

In certain examples, the processes for making a compound of Formula (I) include, prior to contacting a compound of Formula (Ic) with a compound of Formula (Id) to make a compound of Formula (I), isolating a stereoisomer of a compound of Formula (Ic) from a mixture of stereoisomers of compounds of Formula (Ic). In these examples, the mixture of mixture of stereoisomers of compounds of Formula (Ic) may be provided by a commercial source or generated in-situ.

In some examples, step (1) of the process for making a compound of Formula (I) includes contacting a compound of Formula (Ia) with a compound of Formula (Ib) under coupling conditions to form a compound of Formula (Ic) as follows:

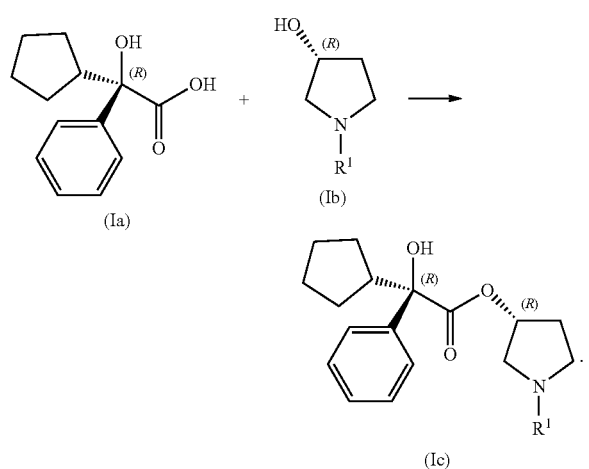

In some of these examples, R¹ is alkyl. In other examples, R¹ is methyl, ethyl, n-propyl, i-propyl, n-butyl, t-butyl, i-butyl, n-pentyl, or i-pentyl. In some examples, R¹ is methyl or ethyl. In some other examples, R¹ is methyl. In other examples, R¹ is ethyl.

In certain examples, the processes for making a compound of Formula (I) include, in step (1) contacting a compound of Formula (Ia-1) with a compound of Formula (Ib-1) under coupling conditions to form a compound of Formula (Ic-1) as follows:

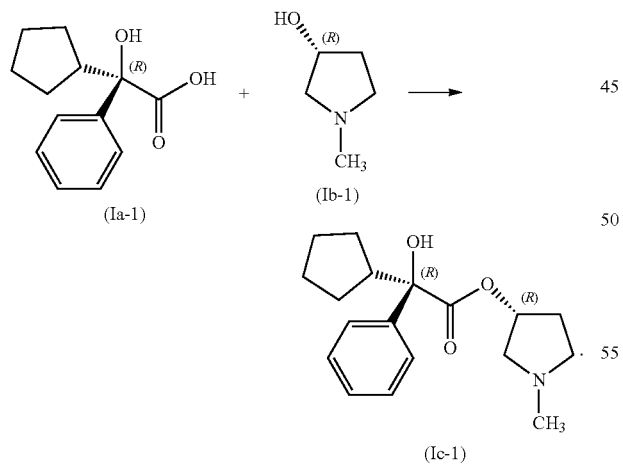

In some examples, the processes for making a compound of Formula (I) include, in step (1), providing stereomerically pure compounds of Formula (Ia) and Formula (Ib).

In any of the examples of the processes for making a compound of Formula (I) include, the compound of Formula (I) can include the following structures (Ia1) or (Ia2):

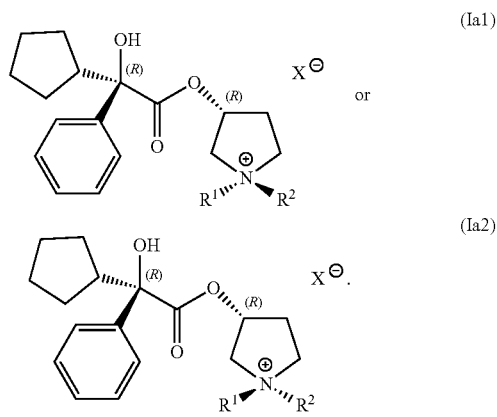

In some examples, the compound of Formula (Ia1) is present in a greater concentration than is a compound of Formula (Ia2).

In some other examples, the compound of Formula (Ia2) is present in a greater concentration than is a compound of Formula (Ia1).

In some examples, the compound of Formula (I) comprises a mixture of compounds having the following structures:

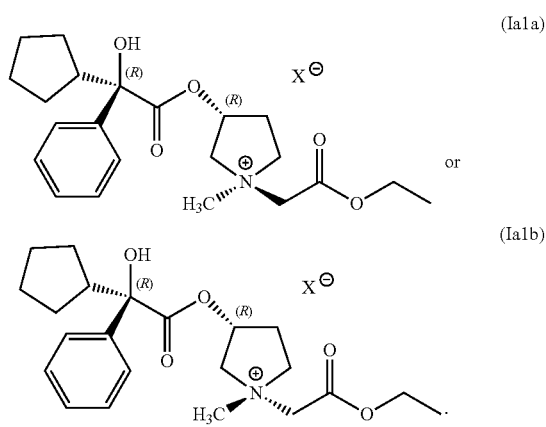

In some examples, R¹ and R² are selected so that the pyrrolidinyl nitrogen atom has (S) stereochemistry about its nitrogen atom. In some of these examples, the compound of Formula (I) is the following:

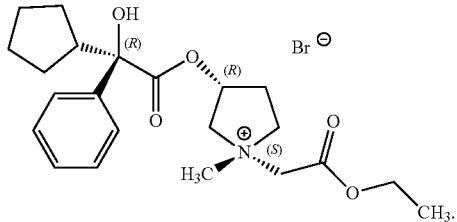

In some examples, R¹ and R² are selected so that the pyrrolidinyl nitrogen atom has (R) stereochemistry about its nitrogen atom. In some examples, the compound of Formula (I) is the following:

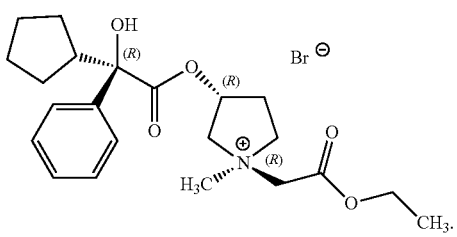

In some examples of the processes for making a compound of Formula (I), in step (1) a compound of Formula (Ib-s) is present in addition to a compound of Formula (Ib):

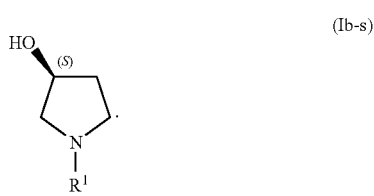

In some examples, the processes for making a compound of Formula (I) result in a yield of a compound of Formula (I) is at least 30%. In some examples, the yield is at least 35%, 40%, 45%, 50%, 55%, 60%, 65%, 70%, 75%, 80%, 85%, 90%, or 95%.

In some examples, the processes for making a compound of Formula (I) include isolating compound (Ic) from a mixture of compound (Ic) and its stereoisomers using chiral resolution agents and salts. In some examples, the processes include using various salts, various acids, or combinations thereof, to separate stereoisomers, e.g., diastereoisomers. In certain examples, the acid is a nitroisophthalic acid.

In some examples, the isolating step includes the isolating processes set forth in Finnish Patent Application No. 1495/75 which issued Sep. 10, 1975 as Finnish Patent 49713. Finnish Patent Application No. 1495/75 and Finnish Patent 49713 sets forth processes for making erythro-1-methyl-3-pyrrolidinyl-alpha-cyclopentylmandelate methyl bromide. For example, generally, a mixture of compound (Ic) and its stereoisomers can be converted to nitroisophthalic acid salt derivatives. Each isomer salt derivative can then be crystallized. Each isomer salt has a different solubility. By using the difference in solubilities of these salts, these nitroisophthalic acid salt derivatives of a mixture of compound (Ic) and its stereoisomers can each be separated from each other. Once separated from each other, the nitrophthalic acid salt moiety can be removed from the nitrophthalic salt derivative compound using an inorganic base. As set forth in Finnish Patent Application No. 1495/75 and Finnish Patent 49713, the erythro (RR/SS) and threo (RS/SR) enantiomeric pairs of compound (Ic) can be separated from each other by a nitroisophthalate salt process. The technique relies on the lower solubility of the 5-nitroisophthalate salt of the threo pair as compared to the erythro pair. As set forth in Finnish Patent Application No. 1495/75 or Finnish Patent 49713, the threo salts crystallize preferentially leaving the salt of the erythro pair in solution. By separating the solution from the solid crystal, the erythro (RR/SS) and threo (RS/SR) enantiomeric pairs of compound IIIc (e.g., IIIc-1) can be separated. The stereoisomer resolution techniques from Finnish Patent Application No. 1495/75 or from Finnish Patent 49713 are herein incorporated by reference in their entirety for all purposes.

In any of the above processes, $R^1$ can include alkyl. In any of the above processes, $R^1$ can include methyl, ethyl, n-propyl, i-propyl, n-butyl, t-butyl, i-butyl, n-pentyl, or i-pentyl. In any of the above processes, $R^1$ can include methyl or ethyl. In any of the above processes, $R^1$ can include methyl. In any of the above processes, $R^1$ can include ethyl.

In any of the above processes, X can be a halide. For example, X can include F⁻, Cl⁻, Br⁻, I⁻ or combinations thereof. In some examples, X is Br⁻.

In any of the above processes, $R^2$ can include alkyl. In any of the above processes, $R^2$ can include methyl, ethyl, n-propyl, i-propyl, n-butyl, t-butyl, i-butyl, n-pentyl, or i-pentyl. In any of the above processes, $R^2$ can include methyl or ethyl. In any of the above processes, $R^1$ can include methyl. In any of the above processes, $R^2$ can include ethyl.

In any of the above processes, $R^1$ can include alkyl substituted with alkoxycarbonyl and $R^2$ as alkyl.

In any of the above processes, $R^1$ can include alkyl substituted with alkoxycarbonyl and $R^2$ as methyl.

In any of the above processes, $R^1$ can include —$CH_2C(O)OCH_2CH_3$ and $R^2$ as alkyl.

In any of the above processes, $R^1$ can include $R^1$—$CH_2C(O)OCH_2CH_3$ and $R^2$ as methyl. In some examples, $R^1$ is —$CH_2C(O)OCH_2CH_3$ and $R^2$ is methyl.

In some examples herein, the compound of Formula (Ia) is compound (4):

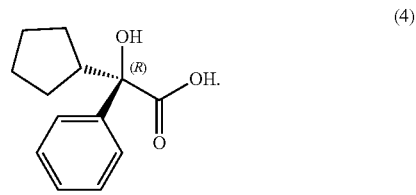

In some examples herein, the compound of Formula (Ib) is compound (7):

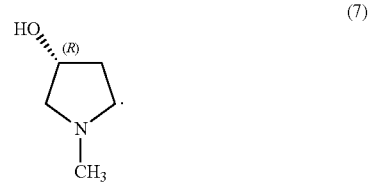

In some examples herein, the compound of Formula (Ic) is compound (8):

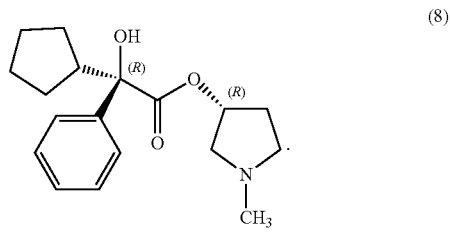

In some examples herein, the compound of Formula (I) is the following compound:

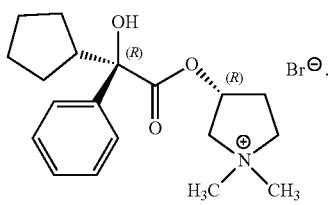

In some examples herein, the compound of Formula (I) is compound (9):

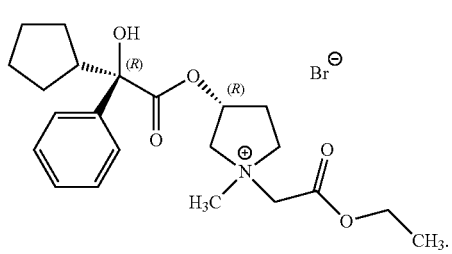
(9)

In some examples herein, the compound of Formula (Id) is the following compound:

In some examples herein, the compound of Formula (Id) is compound (10):

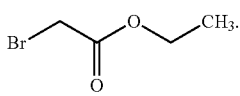
(10)

In some examples herein, the compound of Formula (Ia) is compound (4):

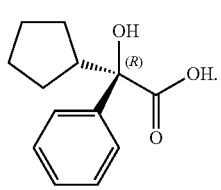
(4)

In some examples, compound (4) is made by contacting compound (3):

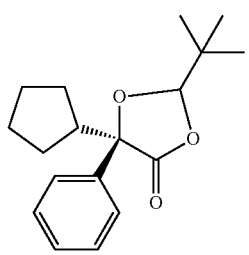
(3)

with a methanolic base. In some examples, compound (4) is made by contacting compound (3):

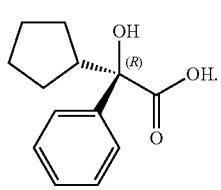
(3)

with a base in methanol. In some examples, this methanolic base is selected from methanolic alkali or alkaline earth hydroxide bases. In certain examples, the methanolic base is KOH in methanol. In some examples, this methanolic base is selected from an alkali or alkaline earth hydroxide base in methanol.

In some examples herein, the compound of Formula (Ia) is compound (4):

(4)

In some examples, compound (4) is made by contacting compound (3):

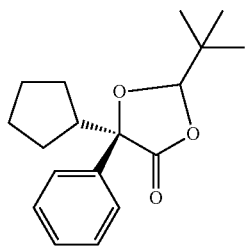
(3)

with methanolic potassium hydroxide.

In some of these examples the contacting of compound (3) with methanolic potassium hydroxide is at about 65° C. In some of these examples the contacting of compound (3) with methanolic potassium hydroxide is at about 50° C. to about 80° C. In some of these examples the contacting of compound (3) with methanolic potassium hydroxide is at about 50° C. In some of these examples the contacting of compound (3) with methanolic potassium hydroxide is at about 55° C. In some of these examples the contacting of compound (3) with methanolic potassium hydroxide is at about 60° C. In some of these examples the contacting of compound (3) with methanolic potassium hydroxide is at about 65° C. In some examples, the processes further include cooling compound (4). In some examples, the processes further include removing the methanol from the methanolic potassium hydroxide. In some examples, the processes further include adding an acid and extracting compound (4) with an organic solvent. In some examples, the acid is HCl and the organic solvent is ethyl acetate. In some examples, the solvents include any mineral acid. In some examples, the solvents include a phosphate buffer. In some examples, the solvents include an ammonium chloride solution. In some examples, the solvents include sulfuric acids, phosphoric acids, ammonium chloride solutions, monobasic sodium, potassium phosphate (e.g., $NaH_2PO_4$) solutions, or combinations thereof. In some examples, the sulfuric acid is $H_2SO_4$. In some other examples, the phosphoric acid is $H_3PO_4$ In some examples, compound (4) is made by contacting compound (3):

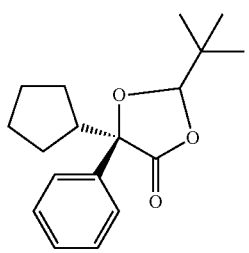

(3)

with a methanolic base according to a step described in Grover et al. in J. Org. Chem. 65: 6283-6287 (2000). In some examples, dioxalan-4-one is reacted with KOH in MeOH to form the S-enantiomer of cyclopentylmandelic acid (CPMA). In some examples, about 50 mL dioxalan-4-one is reacted with about 270 mmols KOH in 100 mL MeOH to form the S-enantiomer of cyclopentylmandelic acid (CPMA).

In some examples of making compound (4), the processes include crystallizing the compound (4). In some examples, compound (3) is made by contacting compound (2) with an alkali metal amide and cyclopentyl bromide. In some examples, the alkali metal amide is selected from lithium diisopropyl amide (LDA), lithium bis(trimethylsilyl)amide (LiHMDS), sodium bis(trimethylsilyl)amide (NaHMDS), or potassium bis(trimethylsilyl)amide (KHMDS). In some examples, the alkali metal amide is lithium diisopropyl amide (LDA). In some examples, the alkali metal amide is sodium bis(trimethylsilyl)amide (NaHMDS). In some examples, the alkali metal amide is potassium bis(trimethylsilyl)amide (KHMDS).

In some examples, compound (3) is made by contacting compound (2) with LiHMDS and cyclopentyl bromide.

In some examples, compound (3) is made by contacting compound (2) with LiHMDS at −78° C., using lithium bis-(trimethylsilyl)amide in hexane solution (e.g., 1.0 M in hexane), followed by stirring for 1 h. In some examples, the processes further include adding cyclopentyl bromide (168 mmol). In some examples, the completion of the reaction may be followed by TLC.

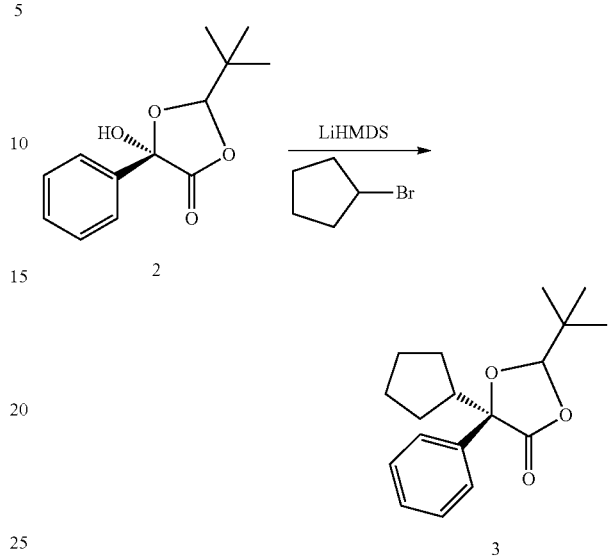

In some examples, compound (2) is made by contacting compound (1) with pivaldehyde to form compound (2).

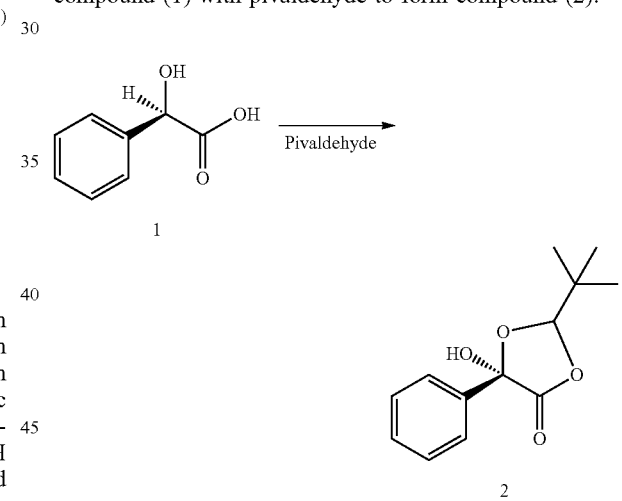

In some examples, the process making compound (2) is carried out in one or more solvents. The solvent(s) can be any solvent deemed suitable to those of skill in the art for carrying out the reaction. In certain embodiments, the solvent(s) does not appreciably react with the compound (1) or pivaldehyde. In certain embodiments, the solvent(s) is selected from alkanes such as, but not limited to, pentane, hexane, n-heptane isomers thereof, and combinations thereof. In some other examples, the solvent is toluene, ethylbenzene, chlorobenzene, xylenes, or combinations thereof. In other examples, the solvent is an ether such as, but not limited to, THF, MeTHF or MTBE. In some examples, the solvent is any combination of the aforementioned solvents.

In particular embodiments, the solvent is hexane.

The concentration of the compounds (1) or pivaldehyde is about 0.1M to about 2M. In some examples, a modest excess of the compounds (1) or pivaldehyde is used. The process for making compound (2) is carried out at any temperature deemed suitable by those of skill in the art. In particular embodiments, the reaction is conducted at any temperature from about 0° C. to about 80° C., from about 10° C. to about 75° C., from about 20° C. to about 65° C., or from about 30° C. to about 55° C. In particular embodiments, the reaction is at room temperature. In particular embodiments, the reaction is at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., or about 85° C.

The process for making compound (2) is carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, or at least about 10,000 L.

The reaction above can proceed for any time deemed suitable for formation of compound (2). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography. In some examples, the processes for making compounds (2) include stirring the reaction, for small laboratory scale production, or agitating the reaction for pilot or large scale commercial production.

The process making compound (2) is carried out in one or more solvents. The solvent(s) can be any solvent deemed suitable to those of skill in the art for carrying out the reaction. In certain embodiments, the solvent(s) does not appreciably react with the compound compounds (1) or pivaldehyde. In particular embodiments, the solvent is hexane. In some examples, the solvent is selected from the group consisting of ethers, esters, aromatics, alkanes, chlorinated solvents and ketones. In some examples, the solvent is selected from the group consisting of N-methyl-pyrrolidone (NMP), dimethyl formamide (DMF) and dimethylacetamide (DMAC). In some examples, when the solvent is an ether, the solvent is selected from tetrahydrofuran (THF), methyl tetrahydrofuran (MeTHF), methyl tert-butyl ethyl (MTBE), and combinations thereof. In some examples, when the solvent is an ester, the solvent is selected from ethyl acetate, isopropyl acetate, and combinations thereof. In some examples, when the solvent is an aromatic, the solvent is selected from toluene, chlorobenzene, xylenes, and combinations thereof. In some examples, when the solvent is an alkane, the solvent is selected from pentane, hexane, heptane, and combinations thereof. In some examples, when the solvent is a chlorinated solvent, the solvent is selected from dichloromethane, chloroform, and combinations thereof. In some examples, when the solvent is a ketone, the solvent is selected from methyl ethyl ketone (MEK). In some examples, the solvent in a combination of any of the aforementioned solvents. In some examples, the solvent is a combination of any of the above ethers, esters, aromatics, alkanes, chlorinated solvents and ketone solvents. In some examples, the solvent is selected from NMP, DMF, DMAC, THF, MeTHF, MTBE, ethyl acetate, isopropyl acetate, toluene, chlorobenzene, xylenes, pentane, hexane, heptane, dichloromethane, chloroform, methyl ethyl ketone, and combinations thereof. In some examples, the solvent includes NMP, DMF, DMAC, THF, MeTHF, MTBE, ethyl acetate, isopropyl acetate, toluene, chlorobenzene, xylenes, pentane, hexane, heptane, dichloromethane, chloroform, methyl ethyl ketone, or combinations thereof.

The process for making compound (2) is carried out at any temperature deemed suitable by those of skill in the art. In particular embodiments, the reaction is conducted at any temperature from about 0° C. to about 80° C., from about 10° C. to about 75° C., from about 20° C. to about 65° C., or from about 30° C. to about 55° C. In particular embodiments, the reaction is at room temperature. In particular embodiments, the reaction is at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., or about 85° C.

The method of making compound (2) is carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, or at least about 10,000 L The reaction above can proceed for any time deemed suitable for formation of compound (2). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography.

In some examples, the reaction is monitored by observing the consumption of reagents by TLC.

The method making compound (3) is carried out in hexane. The solvent(s) can be any solvent deemed suitable to those of skill in the art for carrying out the reaction. In certain embodiments, the solvent(s) does not appreciably react with the compound (2), LiHMDS, or cyclopropyl-bromide. In particular embodiments, the solvent is hexane.

In some examples, the solvent is selected from the group consisting of ethers, esters, aromatics, alkanes, chlorinated solvents and ketones. In some examples, the solvent is selected from the group consisting of N-methyl-pyrrolidone (NMP), dimethyl formamide (DMF) and dimethylacetamide (DMAC). In some examples, when the solvent is an ether, the solvent is selected from tetrahydrofuran (THF), methyl tetrahydrofuran (MeTHF), methyl tert-butyl ethyl (MTBE), and combinations thereof. In some examples, when the solvent is an ester, the solvent is selected from ethyl acetate, isopropyl acetate, and combinations thereof. In some examples, when the solvent is an aromatic, the solvent is selected from toluene, chlorobenzene, xylenes, and combinations thereof. In some examples, when the solvent is an alkane, the solvent is selected from pentane, hexane, heptane, and combinations thereof. In some examples, when the solvent is a chlorinated solvent, the solvent is selected from dichloromethane, chloroform, and combinations thereof. In some examples, when the solvent is a ketone, the solvent is selected from methyl ethyl ketone (MEK). In some examples, the solvent in a combination of any of the aforementioned solvents. In some examples, the solvent is a combination of any of the above ethers, esters, aromatics, alkanes, chlorinated solvents and ketone solvents. In some examples, the solvent is selected from NMP, DMF, DMAC, THF, MeTHF, MTBE, ethyl acetate, isopropyl acetate, toluene, chlorobenzene, xylenes, pentane, hexane, heptane, dichloromethane, chloroform, methyl ethyl ketone, and combinations thereof. In some examples, the solvent includes NMP, DMF, DMAC, THF, MeTHF, MTBE, ethyl acetate, isopropyl acetate, toluene, chlorobenzene, xylenes, pentane, hexane, heptane, dichloromethane, chloroform, methyl ethyl ketone, or combinations thereof.

The process for making compound (3) is preferably carried out with a base. In particular embodiments, the base is selected from the group consisting of sodium hydroxide and potassium hydroxide.

The concentration of the compounds (2), LiHMDS, or cyclopropyl-bromide is about 0.01M to about 2M. The process for making compound (3) is carried out at any temperature deemed suitable by those of skill in the art. In some examples, the reaction is initiated at low temperatures, e.g., −78° C. or about −70 to −80° C. In some examples, the reaction is slowly warmed slowly to room temperature with continuous stirring. In particular embodiments, the reaction is conducted at any temperature from about −80° C. to about 25° C., from about −70° C. to about 25° C., from about −60° C. to about 25° C., or from about −50° C. to about 25° C. The process for making compound (3) is carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, or at least about 10,000 L. The reaction above can proceed for any time deemed suitable for formation of compound (3). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography. In some examples, the reaction is monitored by observing the consumption of reagents by TLC.

In some examples, the compound of Formula (Ib) is compound (7):

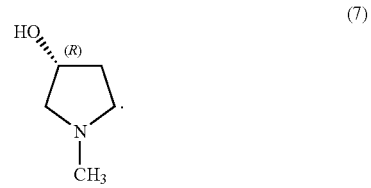

(7)

In some examples, compound (7) is made by contacting compound (6) with a reducing agent:

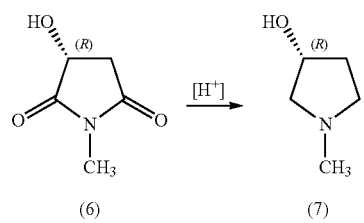

The method making compound (7) may be carried out in one or more aprotic non-halogenated solvents. In other examples, the solvent(s) can be any solvent deemed suitable to those of skill in the art for carrying out the reaction. In certain embodiments, the solvent(s) is selected from the group consisting of hydrocarbon solvents such as, but not limited to, pentane(s), hexane(s), heptane(s), aromatic hydrocarbon solvents such as, but not limited to, toluene, xylene(s), ether solvents such as, but not limited to, THF, MTBE, methyl-THF, and combinations thereof. In particular embodiments, the solvent is a mixture of toluene and THF. For, instance, the solvent can be 50% toluene v/v and 50% THF v/v. In particular embodiments, the solvent is toluene.

In some examples, the solvent is selected from the group consisting of ethers, esters, aromatics, alkanes, and ketones. In some examples, the solvent is selected from the group consisting of N-methyl-pyrrolidone (NMP), dimethyl formamide (DMF) and dimethylacetamide (DMAC). In some examples, when the solvent is an ether, the solvent is selected from tetrahydrofuran (THF), methyl tetrahydrofuran (MeTHF), methyl tert-butyl ethyl (MTBE), and combinations thereof. In some examples, when the solvent is an ester, the solvent is selected from ethyl acetate, isopropyl acetate, and combinations thereof. In some examples, when the solvent is an aromatic, the solvent is selected from toluene, xylenes, and combinations thereof. In some examples, when the solvent is an alkane, the solvent is selected from pentane, hexane, heptane, and combinations thereof. In some examples, when the solvent is a ketone, the solvent is selected from methyl ethyl ketone (MEK). In some examples, the solvent in a combination of any of the aforementioned solvents. In some examples, the solvent is a combination of any of the above ethers, esters, aromatics, alkanes, and ketone solvents. In some examples, the solvent is selected from NMP, DMF, DMAC, THF, MeTHF, MTBE, ethyl acetate, isopropyl acetate, toluene, xylenes, pentane, hexane, heptane, methyl ethyl ketone, and combinations thereof. In some examples, the solvent includes NMP, DMF, DMAC, THF, MeTHF, MTBE, ethyl acetate, isopropyl acetate, toluene, xylenes, pentane, hexane, heptane, methyl ethyl ketone, or combinations thereof.

The process for making compound (7) is preferably carried out with a reducing agent.

The concentration of the compounds (6) is about 0.1M to about 2M. The process for making compound (7) is carried out at any temperature deemed suitable by those of skill in the art. In particular embodiments, the reaction is conducted at any temperature from about 0° C. to about 80° C., from about 10° C. to about 75° C., from about 20° C. to about 65° C., or from about 30° C. to about 55° C. In particular embodiments, the reaction is at room temperature. In particular embodiments, the reaction is at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., or about 85° C.

The process for making compound (7) is carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, at least about 10,000 L, at least about 25,000 L, at least about 50,000 L, at least about 75,000 L, or at least about 10,000 L.

The reaction above can proceed for any time deemed suitable for formation of compound (7). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography.

The processes herein may further include stirring or agitating as the reaction proceeds.

In some examples, compound (6) is made by contacting R(−)-malic acid, compound (5), with methyl amine:

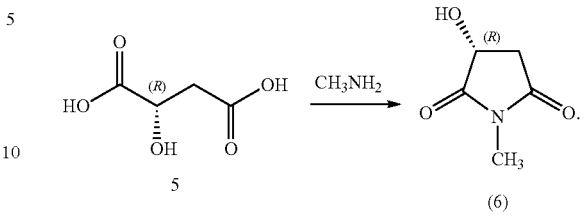

The method making compound (6) is carried out in one or more solvents. The solvent(s) can be any solvent deemed suitable to those of skill in the art for carrying out the reaction. In certain embodiments, the solvent(s) does not appreciably react with the compound (5) or methyl-amine. In certain embodiments, the solvent(s) allows the azeotropic removal of water but does not participate in the reaction. In certain embodiments, the solvent(s) is selected from toluene.

The concentration of the compounds (5) or methyl-amine is about 0.1M to about 2M. In some examples, a slight excess of methylamine is used to avoid the formation of the diamide over the imide. In some examples, the excess amount of methylamine is 10-20% molar excess.

The process for making compound (5) is carried out at any temperature deemed suitable by those of skill in the art. In particular embodiments, the reaction is conducted at any temperature from about 0° C. to about 80° C., from about 10° C. to about 75° C., from about 20° C. to about 65° C., or from about 30° C. to about 55° C. In particular embodiments, the reaction is at room temperature. In particular embodiments, the reaction is at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., or about 85° C.

The process for making compound (5) is carried out in any volume deemed suitable by those of skill in the art and depends on the size of the reaction. In particular embodiments, the reaction volume is at least about 50 mL, at least about 100 mL, at least about 150 mL, at least about 200 mL, at least about 225 mL, at least about 250 mL, at least about 500 mL, at least about 1 L, at least about 2 L, at least about 3 L, at least about 4 L, or at least about 5 L. In another embodiment, the reaction volume is at least about 200 mL to at least about 10,000 L. In another embodiment, the reaction volume is at least about 1000 L, at least about 5000 L, or at least about 10,000 L.

The reaction above can proceed for any time deemed suitable for formation of compound (5). In particular embodiments, the reaction proceeds for about 1 hour, about 2 hours, about 3 hours, about 4 hours, about 5 hours, or about 6 hours. In particular embodiments, the reaction proceeds for about 1 to about 6 hours, in another embodiment about 1 to about 4 hours, in another embodiment about 2 to about 4 hours, in another embodiment about 2.5 to about 3.5 hours. Reaction progress can be monitored by standard techniques such as thin layer chromatography or high-performance liquid chromatography.

In some examples, R(−)-malic acid, compound (5), is made by isolating R(−)-malic acid, compound (5), from a mixture comprising compound (5). In some examples, R(−)-malic acid is sourced commercially.

In some examples, R(−)-malic acid, compound (5), is made by isolating R(−)-malic acid, compound (5), from a racemic mixture comprising compound (5). In some examples, R(−)-malic acid is sourced commercially.

In any of the above reaction steps, the reaction progress can be monitored by standard techniques such as thin layer chromatography, gas chromatography, or high-performance liquid chromatography. In some examples, the reaction is monitored by observing the consumption of reagents by TLC.

C. PROCESS FOR MAKING R-1-METHYL-PYRROLIDIN-3-OL

In certain examples herein, the disclosure sets forth a process for making a compound of Formula (Ib):

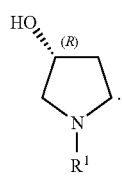

(Ib)

In some examples, $R^1$ is alkyl. In some examples, the processes include providing a compound (5):

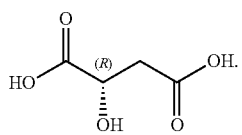

(5)

In some examples, the processes include contacting compound (5) with an alkyl-amine to form a compound of Formula Ibc:

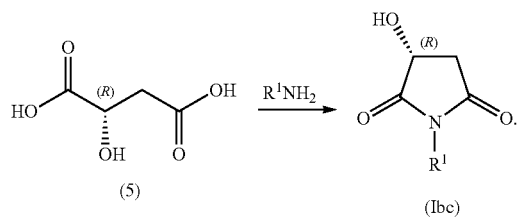

In some examples, the alkylamine is methyl amine and $R^1$ is methyl. In some examples, the processes further include contacting compound (Ibc) with a reducing agent to form a compound of Formula (Ib):

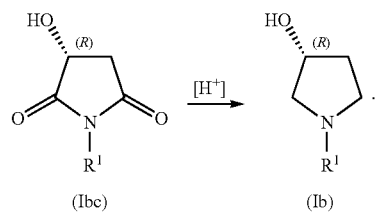

In some examples, $R^1$ is alkyl. In other examples, $R^1$ is methyl, ethyl, n-propyl, i-propyl, n-butyl, t-butyl, i-butyl, n-pentyl, or i-pentyl. In certain examples, $R^1$ is methyl or ethyl. In some examples, $R^1$ is methyl. In certain examples, $R^1$ is ethyl. In some examples, the compound of Formula (Ib) is compound (7):

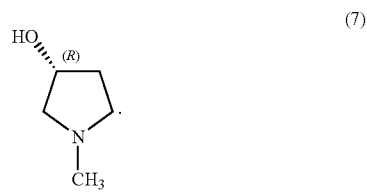

(7)

In some examples, compound (6) is made by contacting R(−)-malic acid, compound (5), with methyl amine:

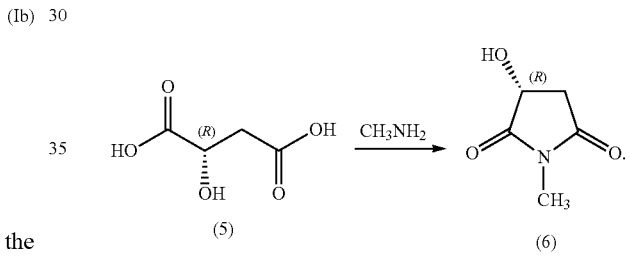

In some of these examples, R(−)-malic acid, compound (5), is made by isolating R(−)-malic acid, compound (5), from a mixture of R(−)-malic acid and L(+)-malic acid. In some other of these examples, R(−)-malic acid, compound (5), is made by isolating R(−)-malic acid, compound (5), from a racemic mixture comprising compound (5).

In certain examples, R-1-methyl-pyrrolidin-3-ol can be prepared according to processes known to those of skill. For example, R-1-methyl-pyrrolidin-3-ol can be prepared using alkyl halides following by chiral resolution of the R-enantiomer. Other useful approaches are set forth in EP 0 269 358. See, also US Patent Application Publication No. 2007/0123557.

D. COMPOUNDS AND PHARMACEUTICAL COMPOSITIONS MADE BY THE PROCESSES SET FORTH HEREIN

In some examples, set forth herein are compounds, mixtures of compounds, mixtures of stereoisomers, or combinations thereof, wherein the compounds, mixtures of compounds, mixtures of stereoisomers are prepared by the processes set forth herein.

In some examples, provided herein are products of the processes above.

In some examples, provided herein are products of the processes for making a compound of Formula (I):

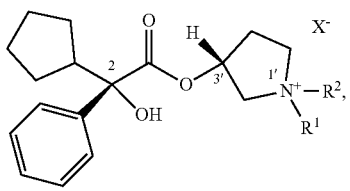
(I)

wherein:
R[1] and R[2] are each, independently in each instance, selected from alkyl and alkyl substituted with alkoxycarbonyl;
the stereochemical configuration about the carbon atom indicated by 2 is R;
the stereochemical configuration about carbon atom indicated by 3' is R; and
X[−] is an anion.

In some examples, provided herein are products of the processes for making a compound of Formula (Ib):

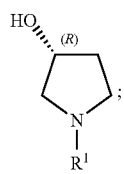
(Ib)

wherein R[1] is selected from the group consisting of alkyl.

In some examples, the carbon indicated by 2 has (R) stereochemistry and the carbon indicated by *3' has (R) stereochemistry. In some examples, R[1] is methyl. In some examples, R[1] is ethyl. In some examples, R[1] is methyl. In some examples, R[1] is —CH$_2$C(O)OCH$_2$CH$_3$.

In some examples, the carbon indicated by 2 has (R) stereochemistry, the carbon indicated by *3' has (R) stereochemistry, and the carbon indicated by *1' has (R) or (S) stereochemistry. In some examples, R[1] is methyl. In some examples, R[1] is ethyl.

In some examples, the carbon indicated by 2 has (R) stereochemistry, the carbon indicated by *3' has (R) stereochemistry, and the carbon indicated by *1' has (R) stereochemistry. In some examples, R[1] is methyl. In some examples, R[1] is ethyl.

In some examples, the carbon indicated by 2 has (R) stereochemistry, the carbon indicated by *3' has (R) stereochemistry, and the carbon indicated by *1' has (S) stereochemistry. In some examples, R[1] is methyl. In some examples, R[1] is ethyl.

In some examples, the compound of Formula (I) is

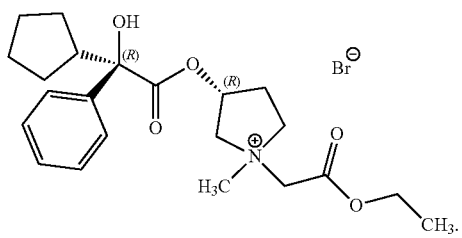

In some examples, the compound of Formula (I) is

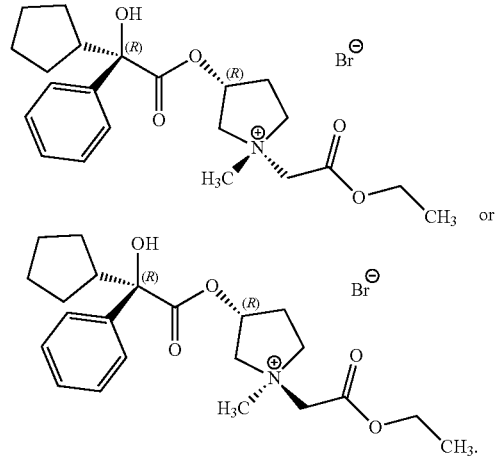

In some examples, the compound of Formula (I) is

![structure]

In some examples, set forth herein is a composition including a mixture of compounds having following structures (Ia1a) and (Ia2b):

![structure]
(Ia1a)

or

![structure]
(Ia1a)

In some examples, the compounds of structures (Ia1) and (Ia2) are prepared by a process set forth herein. In some examples, the compounds are formulated with a pharmaceutically acceptable excipient, diluent, or salt.

In some examples, the compounds of structures (Ia1a) and (Ia2b) are prepared by a method set forth herein. In some examples, the compounds are formulated with a pharmaceutically acceptable excipient, diluent, or salt.

In some examples, set forth herein is a pharmaceutical composition, include a compound prepared by a method set forth herein. In some examples, the composition is formulated as a topical.

In some examples, set forth herein are polymorphs, co-crystals, hydrates and solvates which include a compound prepared by a method set forth herein.

In some examples, set forth herein are polymorphs, co-crystals, hydrates and solvates which include a compound prepared by a process, wherein the process is for making a compound of Formula (I).

In some examples, set forth herein are polymorphs, co-crystals, hydrates and solvates which include a compound prepared by a process, wherein the process is for making a compound of Formula (II).

E. Methods of Using Glycopyrronium Salts

The present disclosure sets forth methods of treating diseases, conditions, or disorders, e.g., hyperhidrosis, including administering a therapeutically effective amount or one or more of the compounds disclosed herein such as, but not limited to, a glycopyrronium compound (e.g. a glycopyrronium salt such as 3'(R)-[R-Cyclopentylphenylhydroxyacetoy]-1'-ethyl-1'methoxycarbonylpyrrolidinium bromide) to a subject in need thereof. Diseases, disorders, and/or conditions include, but are not limited to, those associated with hyperhidrosis or anxiety. Diseases, disorders, and/or conditions include, but are not limited to, any indications for which anticholinergics are therapeutic. In some examples herein, methods of treating diseases, conditions, or disorders include treating gastrointestinal disorders. In some examples herein, methods of treating diseases, conditions, or disorders include treating gastrointestinal disorders selected from gastritis, diarrhea, pylorospasm, diverticulitis, ulcerative colitis, nausea, and vomiting.

In some examples herein, methods of treating diseases, conditions, or disorders include treating genitourinary disorders. In some examples herein, methods of treating diseases, conditions, or disorders include treating genitourinary disorders selected from cystitis, urethritis, and prostatitis.

In some examples herein, methods of treating diseases, conditions, or disorders include treating respiratory disorders. In some examples herein, methods of treating diseases, conditions, or disorders include treating respiratory disorders selected from asthma, chronic bronchitis, and chronic obstructive pulmonary disease (COPD).

In some examples herein, methods of treating diseases, conditions, or disorders include treating sinus bradycardia due to a hypersensitive vagus nerve.

In some examples herein, methods of treating diseases, conditions, or disorders include treating insomnia. In some examples herein, methods of treating diseases, conditions, or disorders include treating insomnia on a short-term basis.

In some examples herein, methods of treating diseases, conditions, or disorders include treating dizziness. In some examples herein, methods of treating diseases, conditions, or disorders include treating vertigo. In some examples herein, methods of treating diseases, conditions, or disorders include ameliorating motion sickness-related symptoms.

In some examples herein, methods of treating diseases, conditions, or disorders include producing antisialagogue effects. In some examples herein, methods of treating diseases, conditions, or disorders include mediating saliva production. In some examples herein, methods of treating diseases, conditions, or disorders include providing a sedative effect.

Herein, subjects include mammals, generally, as well as humans, specifically, but necessarily limited to humans. In some examples, the subject is characterized by a particular patient population, e.g., men, women, adults, children, or persons having a condition such as, but not limited to, hyperhidrosis.

In some examples, set forth herein is a method of treating hyperhidrosis, include administering to a subject in need thereof a composition include a compound prepared by a method set forth herein or a composition set forth herein.

In some examples, set forth herein is a method of treating a disease or disorder marked by a need for an anticholinergic agent, including administering to a subject in need thereof a composition include a compound prepared by a process set forth herein or a composition set forth herein.

In some examples herein, the subject is a mammal. In certain examples, the subject is a human. In certain other examples, the human has hyperhidrosis. In certain other examples, the human suffers from hyperhidrosis.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

The present disclosure includes pharmaceutical compositions of the compounds described herein, e.g., compositions comprising a compound described herein, a salt, stereoisomer, mixture of stereoisomers, polymorph thereof, and a pharmaceutically acceptable carrier, diluent, and/or excipient. Examples of suitable carriers, diluents and excipients include, but are not limited to: buffers for maintenance of proper composition pH (e.g., citrate buffers, succinate buffers, acetate buffers, phosphate buffers, lactate buffers, oxalate buffers and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In another aspect of the invention is a pharmaceutical composition comprising a polymorphic or amorphous form of a compound described herein, including any of the foregoing or hereafter embodiments, and a pharmaceutically acceptable carrier.

The compounds or compositions described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference in its entirety for all purposes.

A pharmaceutical composition can comprise a unit dose formulation, where the unit dose is a dose sufficient to have a therapeutic or suppressive effect or an amount effective to modulate or treat a disease or condition described herein. The unit dose may be sufficient as a single dose to have a therapeutic or suppressive effect or an amount effective to modulate or treat a disease or condition described herein. Alternatively, the unit dose may be a dose administered periodically in a course of treatment or suppression of a disorder, or to modulate or treat a disease or condition described herein.

Pharmaceutical compositions containing the compounds or compositions of the invention may be in any form suitable for the intended method of administration, including, for example, a solution, a suspension, or an emulsion. In some examples, the compositions set forth herein are suitable for topical application. In some examples, liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like.

The compounds or compositions of the invention may be administered topically in dosage unit formulations containing conventional nontoxic pharmaceutically acceptable carriers, adjuvants, and vehicles as desired. For example, suitable modes of administration include transdermal or transmucosal, intranasal (e.g., via nasal mucosa), and the like, and directly to a specific or affected site on the subject. Topical administration may also involve the use of transdermal administration such as transdermal patches or iontophoresis devices. The compounds or compositions are mixed with pharmaceutically acceptable carriers, adjuvants, and vehicles appropriate for the desired route of administration. The compounds described for use herein can be administered in solid form, in liquid form, in aerosol form, or in the form of tablets, pills, powder mixtures, capsules, granules, creams, solutions, emulsions, dispersions, and in other suitable forms. The compounds can also be administered as prodrugs, where the prodrug undergoes transformation in the treated subject to a form which is therapeutically effective. Additional methods of administration are known in the art.

F. EXAMPLES

Unless otherwise stated, chemical reagents were purchased from commercially available sources.

Reagents used herein are available from commercial vendors and were purchased from commercially available sources unless specified herein otherwise or unless the preparation of the reagent(s) is/are described herein.

Example 1

The below synthetic description refers to the numbered compounds illustrated in FIG. 1. Numbers which refer to these compounds in FIG. 1 are bolded and underlined in this Example.

Synthesis of R(−)-Cyclopentylmandelic acid (4)

R(−)-cyclopentylmandelic acid (compound 4) can be synthesized starting with R(−)-mandelic acid (compound 1) according to the scheme in FIG. 1. Compounds 1 and 4 can also be purchased from Sigma-Aldrich.

Step 1: Making Compound 2.

R(−)-mandelic acid (1) was suspended in hexane and mixed with pivaldehyde and a catalytic amount of trifluoromethanesulfonic acid at room temperature to form a mixture. Specifically, R(−)-mandelic acid in hexane suspension (50 g, 328 mmol) was mixed with pivaldehyde (42.7 ml, 396 mmol) then trifluoromethanesulfonic acid (1.23 ml, 14 mmol) at room temperature. The mixture was warmed to 36° C. and then allowed to react for about 5 hours. The reaction was followed by TLC for 5 hours until no starting material could be detected. The mixture was then cooled to room temperature. The mixture was then cooled to room temperature and treated with 8% aqueous sodium bicarbonate. The aqueous layer was removed and the organic layer dried over anhydrous sodium sulfate. After filtration and removal of the solvent under vacuum, the crude product was recrystallized to give (5R)-2-(tert-butyl)-5-phenyl-1,3-dioxolan-4-one (compound 2) in 88% yield (per S-enantiomer yield).

Step 2: Making Compound 3.

Generally, compound 2 was reacted with lithium hexamethyl disilazide (LiHMDS) in hexane at −78° C. under stirring for one hour. Next, cyclopentyl bromide was added to the reaction of compound 2 with LiHMDS. The reaction was kept cool for about four (4) hours and then slowly warmed to room temperature and allowed to react for at least twelve (12) more hours. The resulting mixture was then treated with 10% aqueous ammonium chloride. The aqueous layer was discarded and the organic layer dried over anhydrous sodium sulfate. The solvent was removed under vacuum and the residue recrystallized from hexane to give pure product (5R)-2-(tert-butyl)-5-cyclopentyl-5-phenyl-1, 3-dioxolan-4-one (3) in 63% yield (per S-enantiomer yield). In one specific instance, at −78° C., a lithium bis-(trimethylsilyl)amide in hexane solution (120 ml, 120 mmol, 1.0 M in hexane) was added to compound 2 (25 g, 113.5 mmol, dissolved in 100 ml of dried THF), and stirred for 1 hour, followed by addition of cyclopentyl bromide (25 g, 168 mmol). The reaction was kept at −78° C. for 4 h, then slowly warmed up to room temperature and allowed to react for another 12 hours. The completion of the reaction was followed by TLC. With stirring, a solution of 10% of $NH_4Cl$ (25 ml) was added to the mixture. Then, the mixture was poured into a separation funnel containing 10% $NH_4Cl$ solution (200 ml). The aqueous layer was discarded, and the organic layer was dried over $Na_2SO_4$. The solvent was removed to give a crude product, which was then re-crystallized in hexane to give a pure product (20.36 g, yield 63%, white crystal).

Step 3: Making Compound 4.

R(−)-cyclopentylmandelic acid (compound 4) was prepared by providing compound 3 in aqueous methanolic potassium hydroxide at 65° C. for four hours. After cooling this mixture to room temperature and removing the methanol under vacuum, the aqueous solution was acidified with aqueous hydrochloric acid. The aqueous solution was then extracted twice with ethyl acetate and the organic phase dried with anhydrous sodium sulfate. After removing the solvent and performing a recrystallization, pure R(−)-cyclopentylmandelic acid (compound 4) was obtained in 62% yield (based on S-enantiomer yield).

Synthesis of (R)-1-methylpyrrolidin-3-ol (7)

(R)-1-methylpyrrolidin-3-ol (compound 7) was prepared starting with R(−)-malic acid.

Step 4: Making Compound 6.

R(−)-malic acid (also known as (S)-2-hydroxysuccinic acid) (compound 5) was reacted with methyl amine ($CH_3NH_2$) to form (R)-3-hydroxy-1-methylpyrrolidine-2,5-dione (compound 6). (R)-3-hydroxy-1-methylpyrrolidine-2,5-dione (6) was treated with a reducing agent to form (R)-1-methylpyrrolidin-3-ol (compound 7). In one instance, reduction of compound 6 was performed using $NaAlH_4$/LiCl. To a cooled solution of lithium chloride (0.11 mol) in THF was added $NaAlH_4$ (0.22 mol) in toluene/THF under argon. N-methylsuccinimide (0.083 mol) in THF was added while holding the temperature below 15° C. After the addition was complete, the reaction was allowed to warm to room temperature. After 30 minutes at room temperature, the reaction was heated to greater than 40° C. for 2 hr. The reaction was then cooled to less than 5° C. and toluene (50 ml) was then added. Water (9 ml) was then added slowly holding the temperature below 15° C. Additional $H_2O$ or aqueous NaOH was used as necessary. The insoluble inorganic salts are removed by filtration. These solids are washed with additional THF or toluene to obtain a solution which contained N-methyl pyrrole, as determined by GLC analysis.

Synthesis of 2R3'R-glycopyrrolate base (8)

Step 5: Making Compound 8.

R(−)-cyclopentylmandelic acid (4) was coupled to (R)-1-methylpyrrolidin-3-ol (2) to make the diasterically pure 2R3'R-glycopyrrolate base (compound 8) using 1,1-carbonyldiimideazole (CDI) activated esterification. The R2R3'R-glycopyrrolate base (compound 8) was obtained in greater than 90% yield.

Synthesis of 3'(R)-[R-Cyclopentylphenylhydroxyacetoy]-1'-ethyl-1'methoxycarbonylpyrrolidinium bromide (9)

Step 6: Making Compound 9.

The glycopyrrolate base, compound 8 ((R)-1-methylpyrrolidin-3-yl-
(R)-2-cyclopentyl-2-hydroxy-2-phenylacetate), was treated in dry acetonitrile with methyl bromoacetate at room temperature under stirring for three (3) hours. The crude product was dissolved in a small volume of methylene chloride and poured into dry ethyl ether to obtain a precipitate. This procedure was repeated three times to provide (3R)-3-((R)-2-cyclopentyl-2-hydroxy-2-phenylacetoxy)-1-(2-ethoxy-2-oxoethyl)-1-methylpyrrolidin-1-ium bromide, also known as 3'(R)-[R-Cyclopentylphenylhydroxyacetoy]-1'-ethyl-1'methoxycarbonylpyrrolidinium bromide, (compound 9) in 89% yield.

Example 2

Figure 2:
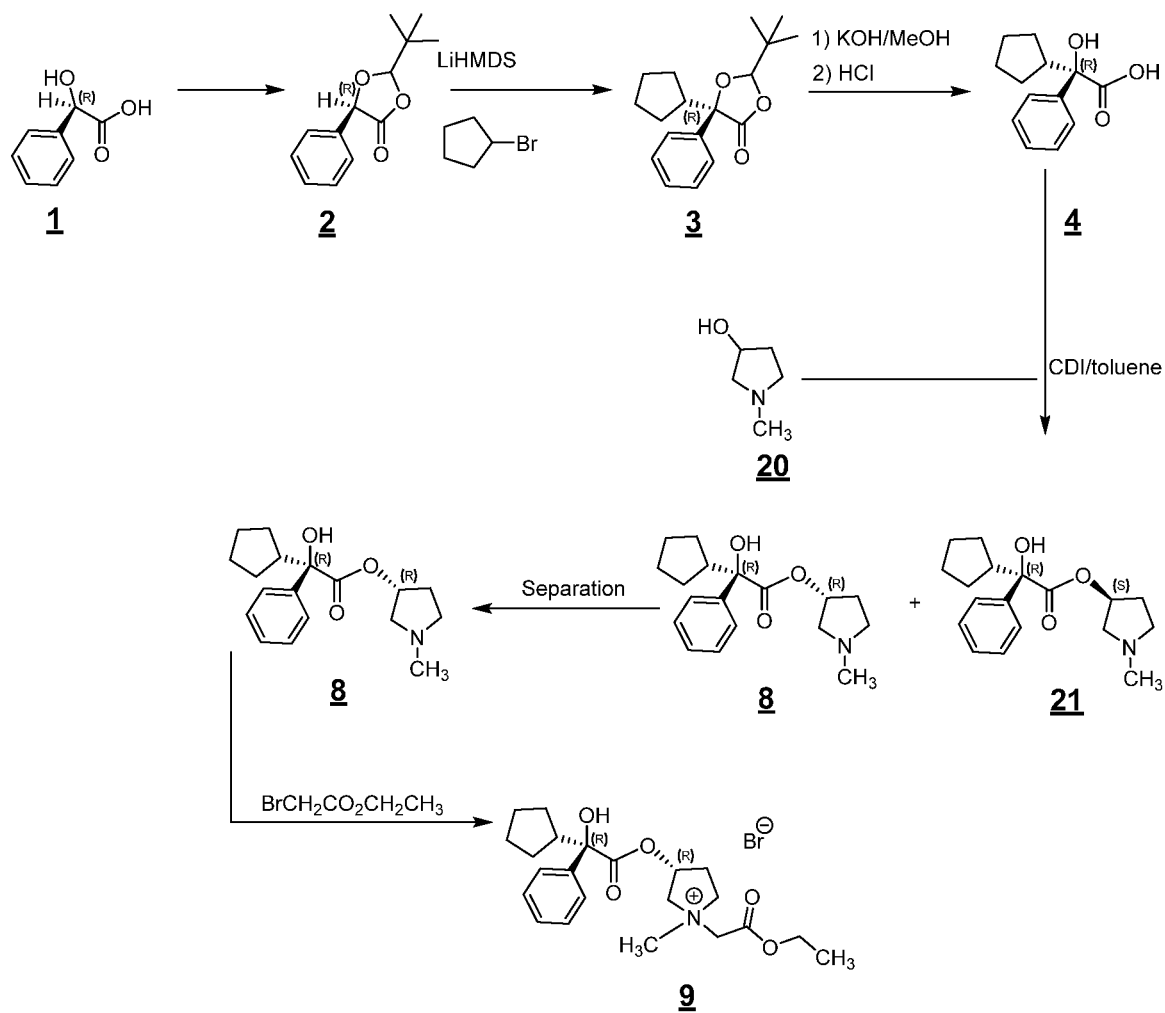
FIG. 2 shows an example synthesis for making a glycopyrronium salt.

The below synthetic description refers to the numbered compounds illustrated in FIG. 2. Numbers which refer to these compounds in FIG. 2 are bolded and underlined in this Example.

Synthesis of R(−)-Cyclopentylmandelic acid (4)

R(−)-cyclopentylmandelic acid (compound 4) can be synthesized starting with R(−)-mandelic acid (compound 1) according to Example 1.

Step 1: Making Compound 2.

R(−)-mandelic acid (1) was suspended in hexane and mixed with pivaldehyde and a catalytic amount of trifluoromethanesulfonic acid at room temperature to form a mixture. The mixture was warmed to 36° C. and then allowed to react for about 5 hours. The mixture was then cooled to room temperature and treated with 8% aqueous sodium bicarbonate. The aqueous layer was removed and the organic layer dried over anhydrous sodium sulfate. After filtration and removal of the solvent under vacuum, the crude product was recrystallized to give (5R)-2-(tert-butyl)-5-phenyl-1,3-dioxolan-4-one (compound 2) in 88% yield (per S-enantiomer yield).

Step 2: Making Compound 3.

Compound 2 was reacted with lithium hexamethyl disilazide (LiHMDS) in hexane at −78° C. under stirring for one hour. Next, cyclopentyl bromide was added to the reaction mixture including compound 2 and LiHMDS. The reaction was kept cool for about four (4) hours and then slowly warmed to room temperature and allowed to react for at least twelve (12) more hours. The resulting mixture was then treated with 10% aqueous ammonium chloride. The aqueous layer was discarded and the organic layer dried over anhydrous sodium sulfate. The solvent was removed under vacuum and the residue recrystallized from hexane to give pure product (5R)-2-(tert-butyl)-5-cyclopentyl-5-phenyl-1,3-dioxolan-4-one (3) in 63% yield (per S-enantiomer yield).

Step 3: Making Compound 4.

R(−)-cyclopentylmandelic acid (compound 4) was prepared by providing compound 3 in aqueous methanolic potassium hydroxide at 65° C. for four hours. After cooling this mixture to room temperature and removing the methanol under vacuum, the aqueous solution was acidified with aqueous hydrochloric acid. The aqueous solution was then extracted twice with ethyl acetate and the organic phase dried with anhydrous sodium sulfate. After removing the solvent and performing a recrystallization, pure R(−)-cyclopentylmandelic acid (compound 4) was obtained in 62% yield (based on S-enantiomer yield).

Next, a racemic mixture of 1-methyl-3-pyrridinol (20) was provided:

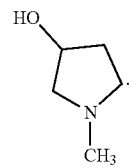

Synthesis of 2R3'R-glycopyrrolate base (8)

Step 4: Making Compound 8.

Enantiomerically pure R(−)-cyclopentylmandelic acid (4) was coupled to racemic 1-methyl-3-pyrridinol (20) using 1,1-carbonyldiimideazole (CDI) activated esterification to make an enantiomerically pure mixture of the following erythro- and threo-glycopyrrolate bases (compounds 8 and 21, respectively):

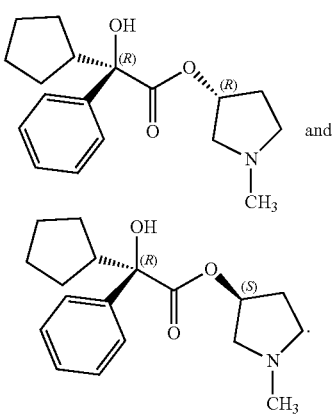

and

The 2R3'R-glycopyrrolate base (compound 8) was then resolved using the 5-nitroisophthalate salt procedure in Finnish Patent 49713, to provide enantiomerically pure 2R3'R (erythro) as well as pure 2R3'S (threo). In this example, the 2R3'S (threo) was discarded. The 2R3'R (erythro) was separated as stereomerically pure compound 8.

Step 6: Making Compound 9.

The glycopyrrolate base, compound 8, was treated in dry acetonitrile with methyl bromoacetate at room temperature under stirring for three (3) hours. The crude product was dissolved in a small volume of methylene chloride and poured into dry ethyl ether to obtain a precipitate. This procedure was repeated three times to provide (3R)-3-((R)-2-cyclopentyl-2-hydroxy-2-phenylacetoxy)-1-(2-ethoxy-2-oxoethyl)-1-methylpyrrolidin-1-ium bromide, also known as 3'(R)-[R-Cyclopentylphenylhydroxyacetoy]-1'-ethyl-1'methoxycarbonylpyrrolidinium bromide (compound 9) in 89% yield. Compound 9 included the following stereoisomers:

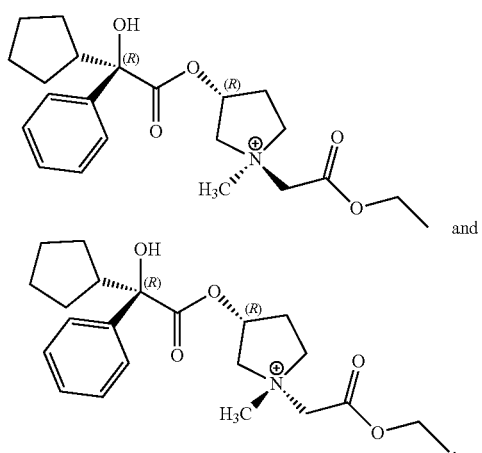

Example 3

The below synthetic description refers to the numbered compounds illustrated in FIG. 3. Numbers which refer to these compounds in FIG. 3 are bolded and underlined in this Example.

Synthesis of S(+)-Cyclopentylmandelic acid (40)

Figure 3:
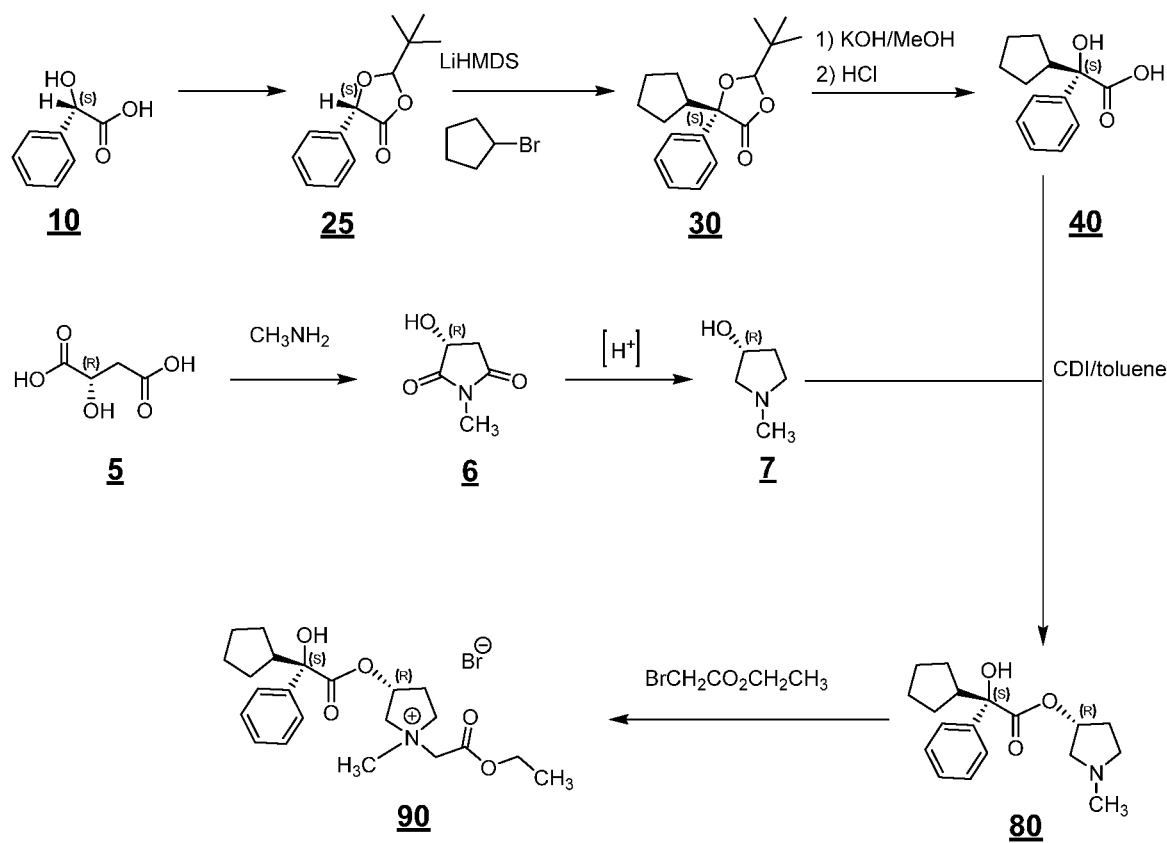
FIG. 3 shows an example synthesis for making a glycopyrronium salt.

S(+)-cyclopentylmandelic acid (compound 40) can be synthesized starting with S(+)-mandelic acid (compound 10) according to the scheme in FIG. 3. Compounds 10 and 40 can be purchased from Sigma-Aldrich.

Step 1: Making Compound 25.

S(+)-mandelic acid (10) was suspended in hexane and mixed with pivaldehyde and a catalytic amount of trifluoromethanesulfonic acid at room temperature to form a mixture. Specifically, S(+)-mandelic acid in hexane suspension (50 g, 328 mmol) was mixed with pivaldehyde (42.7 ml, 396 mmol) then trifluoromethanesulfonic acid (1.23 ml, 14 mmol) at room temperature. The mixture was warmed to 36° C. and then allowed to react for about 5 hours. The reaction was followed by TLC for 5 hours until no starting material could be detected. The mixture was then cooled to room temperature. The mixture was then cooled to room temperature and treated with 8% aqueous sodium bicarbonate. The aqueous layer was removed and the organic layer dried over anhydrous sodium sulfate. After filtration and removal of the solvent under vacuum, the crude product was recrystallized to give cis-(2R, 5S)-2-tert-butyl)-5-phenyl-1, 3-dioxolan-4-one (compound 25) in 88% yield (per S-enantiomer yield).

Step 2: Making Compound 30.

Generally, compound 25 was reacted with lithium hexamethyl disilazide (LiHMDS) in hexane at −78° C. under stirring for one hour. Next, cyclopentyl bromide was added to the reaction of compound 25 with LiHMDS. The reaction was kept cool for about four (4) hours and then slowly warmed to room temperature and allowed to react for at least twelve (12) more hours. The resulting mixture was then treated with 10% aqueous ammonium chloride. The aqueous layer was discarded and the organic layer dried over anhydrous sodium sulfate. The solvent was removed under vacuum and the residue recrystallized from hexane to give pure product (5S)-2-(tert-butyl)-5-cyclopentyl-5-phenyl-1, 3-dioxolan-4-one (30). In one specific instance, at −78° C., a lithium bis-(trimethylsilyl)amide in hexane solution (120 ml, 120 mmol, 1.0 M in hexane) was added to compound 25 (25 g, 113.5 mmol, dissolved in 100 ml of dried THF), and stirred for 1 hour, followed by addition of cyclopentyl bromide (25 g, 168 mmol). The reaction was kept at −78° C. for 4 h, then slowly warmed up to room temperature and allowed to react for another 12 hours. The completion of the reaction was followed by TLC. With stirring, a solution of 10% of NH$_4$Cl (25 ml) was added to the mixture. Then, the mixture was poured into a separation funnel containing 10% NH$_4$Cl solution (200 ml). The aqueous layer was discarded, and the organic layer was dried over Na2SO4. The solvent was removed to give a crude product, which was then re-crystallized in hexane to give a pure product (20.36 g, yield 63%, white crystal).

Step 3: Making Compound 40.

S(+)-cyclopentylmandelic acid (compound 40) was prepared by providing compound 30 in aqueous methanolic potassium hydroxide at 65° C. for four hours. After cooling this mixture to room temperature and removing the methanol under vacuum, the aqueous solution was acidified with aqueous hydrochloric acid. The aqueous solution was then extracted twice with ethyl acetate and the organic phase dried with anhydrous sodium sulfate. After removing the solvent and performing a recrystallization, pure S(+)-cyclopentylmandelic acid (compound 40) was obtained.

Synthesis of (R)-1-methylpyrrolidin-3-ol (7)

(R)-1-methylpyrrolidin-3-ol (compound 7) was prepared starting with R(−)-malic acid.

Step 4: Making Compound 6.

R(−)-malic acid (also known as (S)-2-hydroxysuccinic acid) (compound 5) was reacted with methyl amine (CH$_3$NH$_2$) to form (R)-3-hydroxy-1-methylpyrrolidine-2,5-dione (compound 6)-3-hydroxy-1-methylpyrrolidine-2,5-dione (6) was treated with a reducing agent to form (R)-1-methylpyrrolidin-3-ol (compound 7). In one instance, reduction of compound 6 was performed using NaAlH$_4$/LiCl. To a cooled solution of lithium chloride (0.11 mol) in THF was added NaAlH$_4$ (0.22 mol) in toluene/THF under argon. N-methylsuccinimide (0.083 mol) in THF was added while holding the temperature below 15° C. After the addition was complete, the reaction was allowed to warm to room temperature. After 30 minutes at room temperature, the reaction was heated to greater than 40° C. for 2 hr. The reaction was then cooled to less than 5° C. and toluene (50 ml) was then added. Water (9 ml) was then added slowly holding the temperature below 15° C. Additional H$_2$O or aqueous NaOH was used as necessary. The insoluble inorganic salts are removed by filtration. These solids are washed with additional THF or toluene to obtain a solution which contained N-methyl pyrrole, as determined by GLC analysis.

Synthesis of 2R3'R-glycopyrrolate base (80)

Step 5: Making Compound 8.

S(+)-cyclopentylmandelic acid (40) was coupled to (R)-1-methylpyrrolidin-3-ol (7) to make the diasterically pure 2S3'R-glycopyrrolate base (compound 80) using 1,1-carbonyldiimideazole (CDI) activated esterification. The S2R3'R-glycopyrrolate base (compound 80) was obtained in greater than 90% yield.

Synthesis of 3'(R)-[S-Cyclopentylphenylhydroxyacetoy]-1'-ethyl-1'methoxycarbonylpyrrolidinium bromide (90)

Step 6: Making Compound 90.

The glycopyrrolate base, compound 80, was treated in dry acetonitrile with methyl bromoacetate at room temperature under stirring for three (3) hours. The crude product was dissolved in a small volume of methylene chloride and poured into dry ethyl ether to obtain a precipitate. This procedure was repeated three times to provide (3R)-3-((S)-2-cyclopentyl-2-hydroxy-2-phenylacetoxy)-1-(2-ethoxy-2-oxoethyl)-1-methylpyrrolidin-1-ium bromide, also known as 3' (R)-[S-Cyclopentylphenylhydroxyacetoy]-1'-ethyl-1'methoxycarbonylpyrrolidinium bromide (compound 90).

Example 4

The below synthetic description refers to the numbered compounds illustrated in FIG. 4. Numbers which refer to these compounds in FIG. 4 are bolded and underlined in this Example.

Synthesis of R(−)-Cyclopentylmandelic acid (4)

Figure 4:
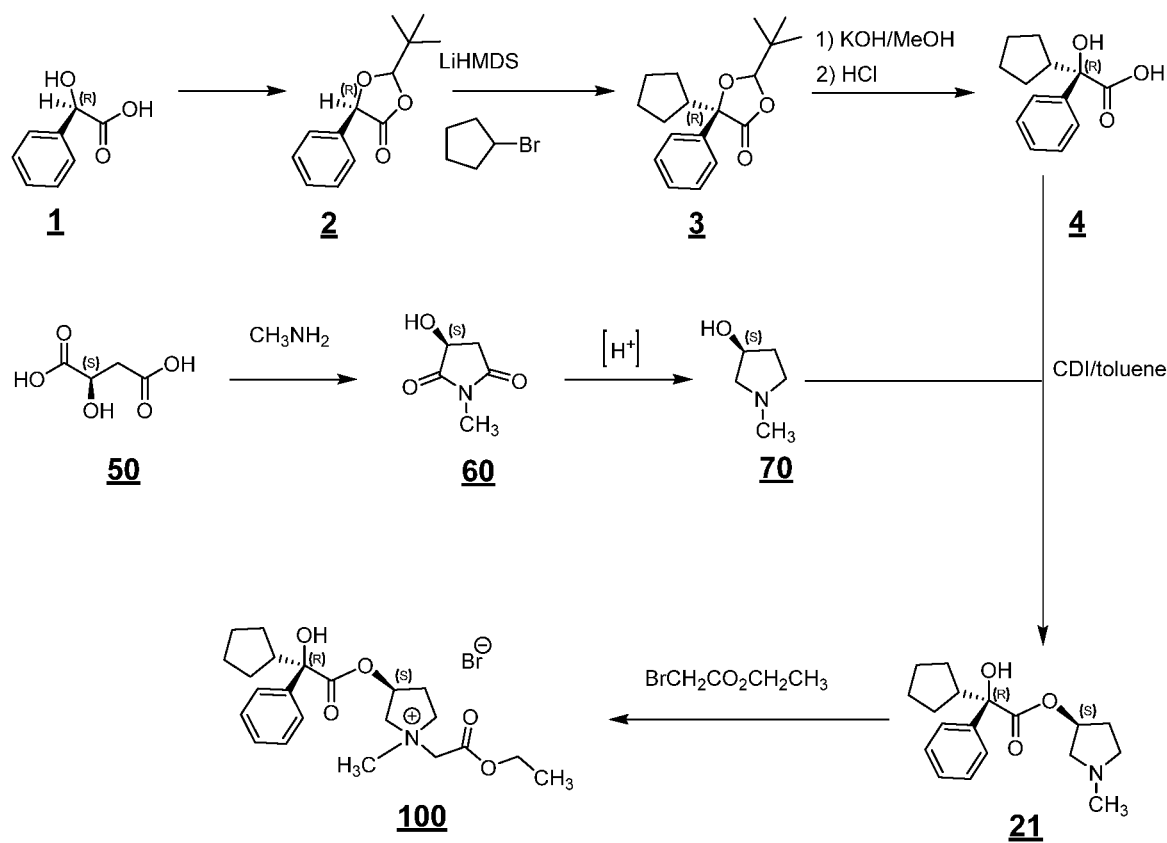
FIG. 4 shows an example synthesis for making a glycopyrronium salt.

R(−)-cyclopentylmandelic acid (compound 4) can be synthesized starting with R(−)-mandelic acid (compound 1) according to the scheme in FIG. 4. Compounds 1 and 4 can also be purchased from Sigma-Aldrich.

Step 1: Making Compound 2.

R(−)-mandelic acid (1) is suspended in hexane and mixed with pivaldehyde and a catalytic amount of trifluoromethanesulfonic acid at room temperature to form a mixture. Specifically, R(−)-mandelic acid in hexane suspension (50 g, 328 mmol) is mixed with pivaldehyde (42.7 ml, 396 mmol) then trifluoromethanesulfonic acid (1.23 ml, 14 mmol) at room temperature. The mixture is warmed to 36° C. and then allowed to react for about 5 hours. The reaction is followed by TLC for 5 hours until no starting material is detected. The mixture is then cooled to room temperature. The mixture is then cooled to room temperature and treated with 8% aqueous sodium bicarbonate. The aqueous layer is removed and the organic layer dried over anhydrous sodium sulfate. After filtration and removal of the solvent under vacuum, the crude product is recrystallized to give (5R)-2-(tert-butyl)-5-phenyl-1,3-dioxolan-4-one (compound 2).

Step 2: Making Compound 3.

Generally, compound 2 is reacted with lithium hexamethyl disilazide (LiHMDS) in hexane at −78° C. under stirring for one hour. Next, cyclopentyl bromide is added to the reaction of compound 2 with LiHMDS. The reaction is kept cool for about four (4) hours and then slowly warmed to room temperature and allowed to react for at least twelve (12) more hours. The resulting mixture is then treated with 10% aqueous ammonium chloride. The aqueous layer is discarded and the organic layer dried over anhydrous sodium sulfate. The solvent is removed under vacuum and the residue recrystallized from hexane to give pure product (5R)-2-(tert-butyl)-5-cyclopentyl-5-phenyl-1,3-dioxolan-4-one (3). In one specific instance, at −78° C., a lithium bis-(trimethylsilyl)amide in hexane solution (120 ml, 120 mmol, 1.0 M in hexane) is added to compound 2 (25 g, 113.5 mmol, dissolved in 100 ml of dried THF), and stirred for 1 hour, followed by addition of cyclopentyl bromide (25 g, 168 mmol). The reaction is kept at −78° C. for 4 hours, then slowly warmed up to room temperature and allowed to react for another 12 hours. The completion of the reaction is followed by TLC. With stirring, a solution of 10% of NH$_4$Cl (25 ml) is added to the mixture. Then, the mixture is poured into a separation funnel containing 10% NH$_4$Cl solution (200 ml). The aqueous layer is discarded, and the organic layer is dried over Na$_2$SO$_4$. The solvent is removed to give a crude product, which is then re-crystallized in hexane to give a pure product.

Step 3: Making Compound 4.

R(−)-cyclopentylmandelic acid (compound 4) is prepared by providing compound 3 in aqueous methanolic potassium hydroxide at 65° C. for four hours. After cooling this mixture to room temperature and removing the methanol under vacuum, the aqueous solution is acidified with aqueous hydrochloric acid. The aqueous solution is then extracted twice with ethyl acetate and the organic phase dried with anhydrous sodium sulfate. After removing the solvent and performing a recrystallization, pure R(−)-cyclopentylmandelic acid (compound 4) is obtained.

Synthesis of (S)-1-methylpyrrolidin-3-ol (70)

(S)-1-methylpyrrolidin-3-ol (compound 70) was prepared starting with S(+)-malic acid.

Step 4: Making Compound 6.

S(+)-malic acid (also known as (R)-2-hydroxysuccinic acid) (compound 50) is reacted with methyl amine (CH$_3$NH$_2$) to form (S)-3-hydroxy-1-methylpyrrolidine-2,5-dione (compound 60). (S)-3-hydroxy-1-methylpyrrolidine-2,5-dione (6) is treated with a reducing agent to form (S)-1-methylpyrrolidin-3-ol (compound 70). In one instance, reduction of compound 60 is performed using NaAlH$_4$/LiCl. To a cooled solution of lithium chloride (0.11 mol) in THF is added NaAlH$_4$ (0.22 mol) in toluene/THF under argon.

N-methylsuccinimide (0.083 mol) in THF is added while holding the temperature below 15° C. After the addition is complete, the reaction is allowed to warm to room temperature. After 30 minutes at room temperature, the reaction is heated to greater than 40° C. for 2 hr. The reaction is then cooled to less than 5° C. and toluene (50 ml) is then added. Water (9 ml) is then added slowly holding the temperature below 15° C. Additional H$_2$O or aqueous NaOH is used as necessary. The insoluble inorganic salts are removed by filtration. These solids are washed with additional THF or toluene to obtain a solution which contained N-methyl pyrrole, as determined by GLC analysis.

Synthesis of threo-glycopyrrolate base:
2R3'S-glycopyrrolate base (21)

Step 5: Making Compound 21.
R(−)-cyclopentylmandelic acid (4) is coupled to (S)-1-methylpyrrolidin-3-ol (70) to make the diasterically pure 2R3'S-glycopyrrolate base (compound 21) using 1,1-carbonyldiimideazole (CDI) activated esterification.

Step 6: Making Compound 100.
The glycopyrrolate base, compound 21, is treated in dry acetonitrile with methyl bromoacetate at room temperature under stirring for three (3) hours. The crude product is dissolved in a small volume of methylene chloride and poured into dry ethyl ether to obtain a precipitate. This procedure is repeated three times to provide (3S)-3-((R)-2-cyclopentyl-2-hydroxy-2-phenylacetoxy)-1-(2-ethoxy-2-oxoethyl)-1-methylpyrrolidin-1-ium bromide, also known as 3'(S)-[R-Cyclopentylphenylhydroxyacetoy]-1'-ethyl-1'methoxycarbonylpyrrolidinium bromide (compound 100).

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:
1. A process for making a compound of Formula (I):

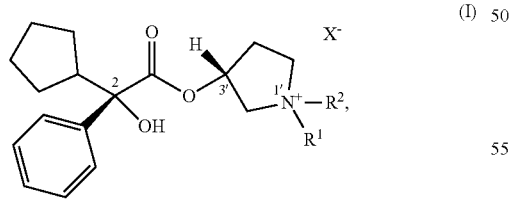

wherein:
R$^1$ and R$^2$ are each, independently in each instance, selected from alkyl and alkyl substituted with alkoxycarbonyl;
the stereochemical configuration about the carbon atom indicated by 2 is R;
the stereochemical configuration about carbon atom indicated by 3' is R;
X$^-$ is an anion;

wherein the process comprises:
contacting compound (1) with pivaldehyde to form compound (2):

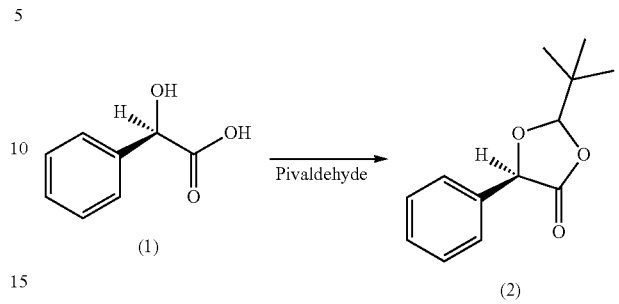

contacting compound (2) with LiHMDS and cyclopentyl bromide to form compound (3):

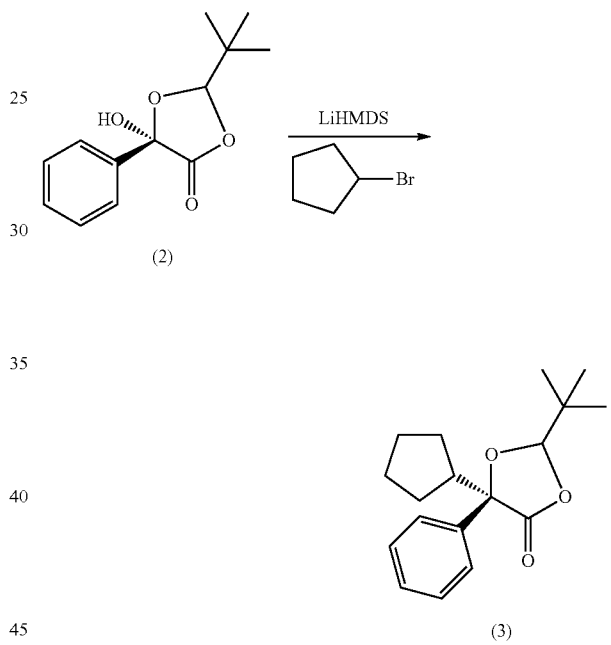

contacting compound (3):

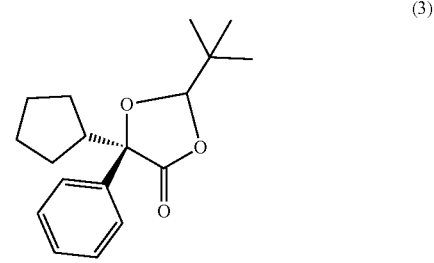 [SMILES: CC(C)(C)C1OC(=O)[C@](c2ccccc2)(C2CCCC2)O1]

with methanolic potassium hydroxide to form a compound (4):

and contacting compound (4) with a compound of Formula (Ib) under coupling conditions to form a compound of Formula (Ic):

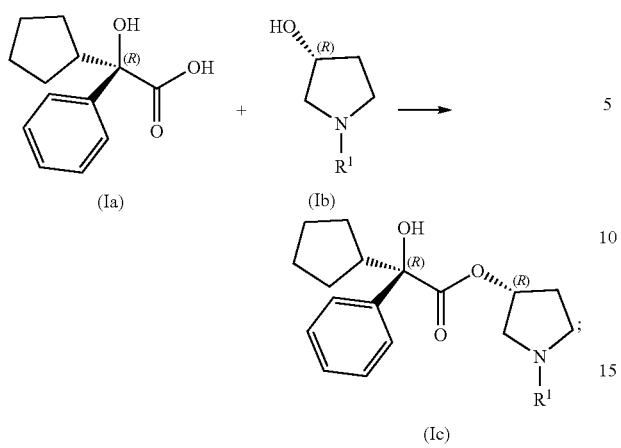

and contacting a compound of Formula (Ic) with a compound of Formula (Id) to make a compound of Formula (I):

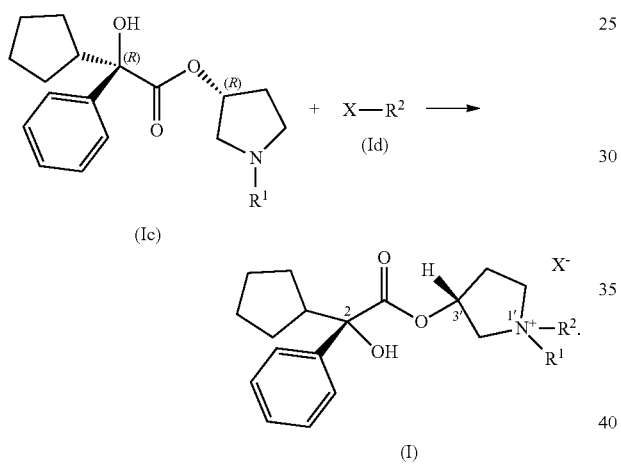

2. The process of claim 1, further comprising:
isolating a stereomerically pure stereoisomer of a compound of Formula (I).

3. The process of claim 2, wherein isolating a stereomerically pure stereoisomer of a compound of Formula (I) is by column chromatography or by simulated moving bed (SMB) separation.

4. The process of claim 1, wherein $R^1$ is alkyl.

5. The process of claim 4, wherein $R^1$ is methyl, ethyl, n-propyl, i-propyl, n-butyl, t-butyl, i-butyl, n-pentyl, or i-pentyl.

6. The process of claim 5, wherein $R^1$ is methyl or ethyl.

7. The process of claim 1, wherein $R^2$ is alkyl.

8. The process of claim 7, wherein $R^2$ is methyl, ethyl, n-propyl, i-propyl, n-butyl, t-butyl, i-butyl, n-pentyl, or i-pentyl.

9. The process of claim 8, wherein $R^2$ is methyl or ethyl.

10. The process of claim 1, wherein $R^1$ is alkyl substituted with alkoxycarbonyl.

11. The process of claim 10, wherein $R^1$—$CH_2C(O)OCH_2CH_3$.

12. The process of claim 11, wherein $R^2$ is methyl.

13. The process of claim 1, wherein during the contacting of compound (4) with a compound of Formula (Ib) under coupling conditions to form a compound of Formula (Ic), compound (4) and Formula (Ib) are stereomerically pure.

14. The process of claim 1, wherein the compound of Formula (I) has the following structure (Ia1) or (Ia2):

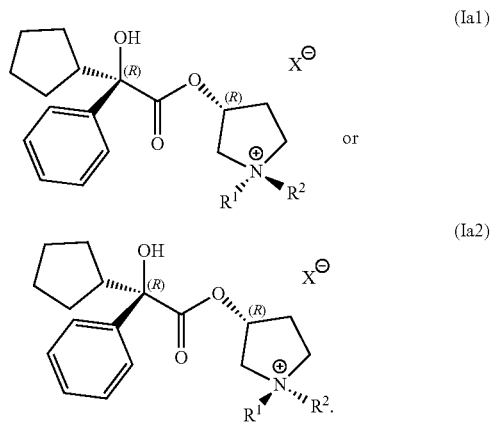

15. The process of claim 1, wherein the compound of Formula (I) comprises a compound having the following structure:

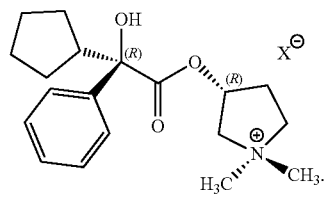

16. The process of claim 1, wherein the compound of Formula (I) comprises a mixture of compounds having the following structures:

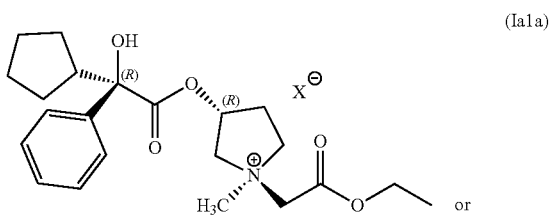

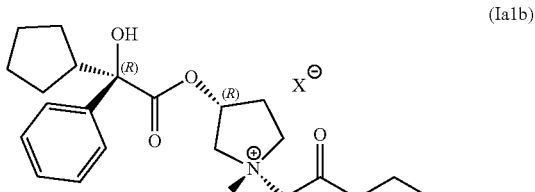

17. The process of claim 1, wherein the compound of Formula (I) is the following:

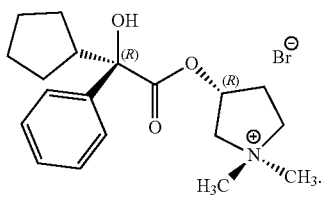

18. The process of claim 1, wherein the compound of Formula (I) is the following:

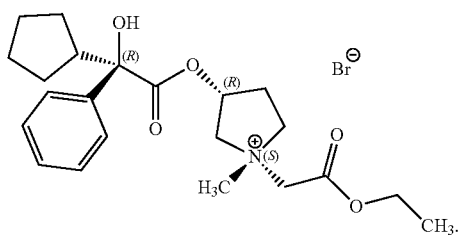

19. The process of claim 1, wherein the compound of Formula (I) is the following:

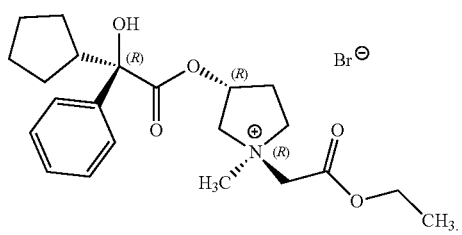

20. The process of claim 1, wherein during the contacting of compound (4) with a compound of Formula (Ib) under coupling conditions to form a compound of Formula (Ic), a compound of Formula (Ib-s) is present:

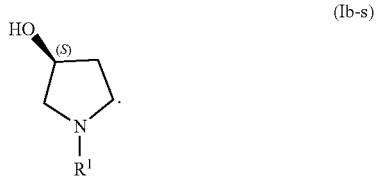

(Ib-s)

21. The process of claim 2, wherein isolating compound (Ic) from a mixture compound (Ic) and its stereoisomers comprises using chiral resolution agents and salts.

22. The process of claim 1, wherein $R^1$ and $R^2$ are both alkyl.

23. The process of claim 1, wherein $X^-$ is halide.

24. The process of claim 23, wherein $X^-$ is selected from the group consisting of $F^-$, $Cl^-$, $Br^-$, $I^-$ and combinations thereof.

25. The process of claim 1, wherein the compound of Formula (Ib) is compound (7):

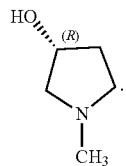

(7)

26. The process of claim 1, wherein the compound of Formula (Ic) is compound (8):

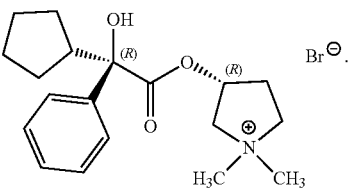

(8)

27. The process of claim 1, wherein the compound of Formula (I) is the following compound:

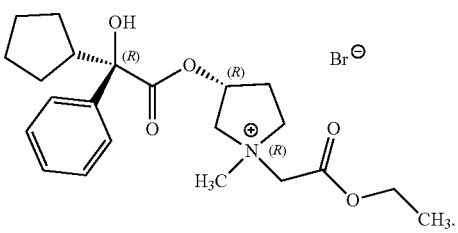

28. The process of claim 1, wherein the compound of Formula (I) is compound (9):

(9)

29. The process of claim 1, wherein the compound of Formula (Id) is the following compound:

Br—CH₃.

30. The process of claim 1, wherein the compound of Formula (Id) is the following compound:

(10)

31. The process of claim 1, comprising crystallizing the compound (4).

32. The process of claim 1, wherein the compound of Formula (Ib) is compound (7):

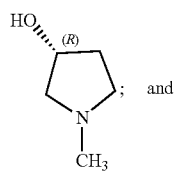

and wherein and the process comprises producing compound (7) by contacting compound (6) with a reducing agent:

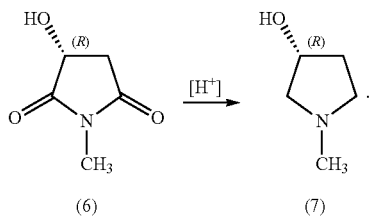

33. The process of claim 32, wherein the process comprises producing compound (6) by contacting R(−)-malic acid, compound (5), with methyl amine:

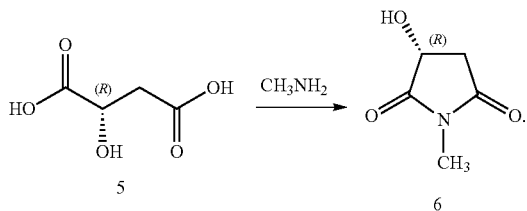

34. A composition comprising a mixture of compounds having following structures (Ia1a) and (Ia1b):

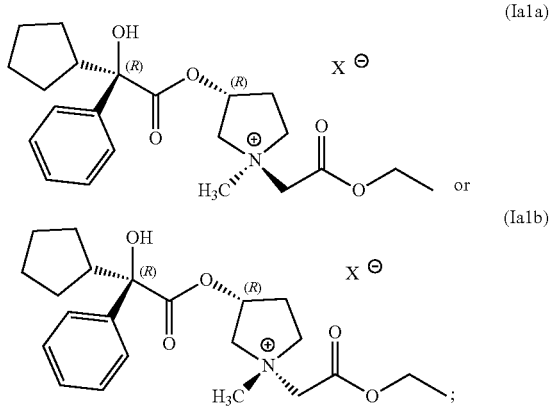

wherein the compounds having structures (Ia1a) and (Ia1b) are prepared by the process of claim 1.

35. A composition comprising a compound having following structure:

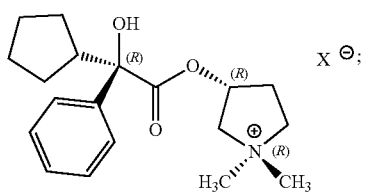

wherein the compound is prepared by the process of claim 1.

36. A method of treating hyperhidrosis, comprising administering to a subject in need thereof a composition comprising a compound prepared by the process of claim 1.

37. A method of treating a disease or disorder marked by a need for an anticholinergic agent, comprising administering to a subject in need thereof a composition comprising a compound prepared by the process of claim 1.

* * * * *